(12) United States Patent
Kreysch et al.

(10) Patent No.: US 7,638,125 B2
(45) Date of Patent: Dec. 29, 2009

(54) PHARMACEUTICAL COMPOSITIONS DIRECTED TO ERB-B1 RECEPTORS

(75) Inventors: Hans-Georg Kreysch, Mainz (DE); Juergen Schmidt, Weiterstadt (DE)

(73) Assignee: Merck Patent GmbH, Darmstadt (DE)

( * ) Notice: Subject to any disclaimer, the term of this patent is extended or adjusted under 35 U.S.C. 154(b) by 113 days.

(21) Appl. No.: 10/530,871

(22) PCT Filed: Oct. 9, 2003

(86) PCT No.: PCT/EP03/11164

§ 371 (c)(1), (2), (4) Date: Apr. 11, 2005

(87) PCT Pub. No.: WO2004/032960

PCT Pub. Date: Apr. 22, 2004

(65) Prior Publication Data

US 2006/0002920 A1 Jan. 5, 2006

(30) Foreign Application Priority Data

Oct. 10, 2002 (EP) .................................. 02022389
Oct. 10, 2002 (EP) .................................. 02022390

(51) Int. Cl.
  *A61K 39/395* (2006.01)
  *A61K 38/19* (2006.01)
  *C12P 21/08* (2006.01)
  *C07K 16/28* (2006.01)
  *C07K 16/30* (2006.01)

(52) U.S. Cl. .............. 424/130.1; 424/133.1; 424/143.1; 435/810; 530/387.1; 530/387.3; 530/388.22; 530/351

(58) Field of Classification Search .............. 530/388.1, 530/388.2, 387.3, 399.1; 424/143.1, 143; 435/810
  See application file for complete search history.

(56) References Cited

U.S. PATENT DOCUMENTS

| | | | |
|---|---|---|---|
| 4,943,533 A * | 7/1990 | Mendelsohn et al. ... | 530/388.22 |
| 5,558,864 A * | 9/1996 | Bendig et al. ............ | 424/133.1 |
| 5,587,458 A | 12/1996 | King et al. | |
| 5,705,157 A * | 1/1998 | Greene .................... | 424/138.1 |
| 5,861,449 A * | 1/1999 | Akitomo et al. ............. | 524/269 |
| 6,217,866 B1 | 4/2001 | Schlessinger et al. | |
| 6,342,219 B1 * | 1/2002 | Thorpe et al. ............ | 424/145.1 |

FOREIGN PATENT DOCUMENTS

| | | |
|---|---|---|
| EP | 0 667 165 | 8/1995 |
| WO | 94 00136 | 1/1994 |
| WO | 02 055106 | 7/2002 |

OTHER PUBLICATIONS

Stryer et al, in Biochemistry, Third edition, W H Freeman Company, New York, pp. 31-33, 1998.*
McInnes et al, Biopoly 43: 339-366, 1997.*
Dermer et al, Bio/Technology 12: 320, 1994.*
Gura et al, Science 278: 1041-1042, Nov 1997.*
Modjtahedi et al, Cell Biophys 22(1-3): 129-146, Jan.-Jun. 1993.*
Ye et al, Oncogene 18: 731-738, 1999.*
Fan et al, Cancer Research 53: 4322-4328, 1993.*
Ciardiello et al, Clinical Cancer Research 5: 909-916, Apr. 1999.*
Gill et al, J Biol Chemistry 259(12): 7755-7760, 1984.*
Mendelsohn et al, Oncogene 19: 6550,6565, 2000.*
Ye D et al: "Augmentation of a Humanized Anti-HER2 MAb 4D5 Induced Growth Inhibition by a Human-Mouse Chimeric Anti-EGF Receptor MAb C225" Oncogene, Basinstoke, Hants, GB, vol. 18, No. 3, Jan. 21, 1999, pp. 731-738.
Kasprzyk P G et al: "Terhapy of an Animal Model of Human Gastric Cancer Using a Combination of Anti-ErbB-2 Monoclonal Antibodies" Cancer Research, Amercian Association for Cancer Research, Baltimore, MD, US, vol. 52, May 15, 1992, pp. 2771-2776.
Dechant et al. "Complement-Dependent Tumor Cell Lysis Triggered by Combinations of Epidermal Growth Factor Receptor Antibodies." *Cancer Research* 68, 4998-5003, Jul. 1, 2008.

* cited by examiner

*Primary Examiner*—Phuong Huynh
(74) *Attorney, Agent, or Firm*—Millen, White, Zelano, Branigan, P.C.

(57) ABSTRACT

The invention relates to pharmaceutical compositions comprising different molecules, preferably monoclonal antibodies, each comprising epitopes that bind simultaneously to different sites within the same ErbB receptor domain, preferably the ErbB1 receptor domain. The preferred antibodies according to this invention are MAb 425 and MAb 225 each in its murine, chimeric and humanized version. The invention relates to the use and methods for an improved treatment of preferably tumors by means of said compositions.

10 Claims, 5 Drawing Sheets

PHARMACEUTICAL COMPOSITIONS DIRECTED TO ERB-B1 RECEPTORS

FIELD OF THE INVENTION

The invention relates to pharmaceutical compositions comprising different biological molecules, preferably monoclonal antibodies, each comprising epitopes that bind simultaneously to different epitopes of the same ErbB receptor domain, especially ErbB1 receptor domain. The preferred antibodies according to this invention are MAb 425 and MAb 225 each in its murine, chimeric and humanized version. The invention relates to the use and methods for an improved treatment of preferably tumors by means of said compositions.

BACKGROUND OF THE INVENTION

Biological molecules, such as monoclonal antibodies (MAbs) or other proteins/polypeptides, as well as small chemical compounds directed against various receptors and other antigens on the surface of tumor cells are known to be suitable for tumor therapy for more than twenty years. With respect to the antibody approach, most of these MAbs are chimerized or humanized to improve tolerability with the human immune system. MAbs or above-mentioned chemical entities specifically bind to their target structures on tumor cells and in most cases also on normal tissues and can cause different effects that dependent on their epitope specificity and/or functional characteristics of the particular antigen. MAbs to orphan receptors or other non-functional cell surface molecules as well as MAbs against structures outside the ligand-binding site of functionally active receptors (e.g. growth factor receptors with kinase activity) would be expected to induce primarily immune effector functions against the target cell (antibody-dependent cell-mediated cytotoxicity (ADCC), complement-dependent cytotoxicity (CDC)). Additionally, depending on the properties of antigen and MAb, binding of the antibody can result in cross-linking of the receptors. Consequent internalization of the receptor-antibody complexes may result in a prolonged down-modulation of the receptor density on the cell surface.

MAbs or small chemical compounds that bind to an epitope within the ligand-binding site or in its direct neighborhood compete for binding of natural ligands to their receptor and thus reduce or completely inhibit ligand binding and can displace already bound ligands from their receptors. This receptor blockade inhibits ligand-dependent receptor activation and downstream signaling. For example, blockade of ErbB receptors, such as the epidermal growth factor receptor (EGFR), by monoclonal antibodies results in various cellular effects including inhibition of DNA synthesis and proliferation, induction of cell cycle arrest and apoptosis as well as antimetastatic and antiangiogenetic effects.

ErbB receptors are typical receptor tyrosine kinases that were implicated in cancer in the 1980s. Tyrosine kinases are a class of enzymes that catalyze the transfer of the terminal phosphate of adenosine triphosphate to tyrosine residues in protein substrates. Tyrosine kinases are believed, by way of substrate phosphorylation, to play critical roles in signal transduction for a number of cell functions. Though the exact mechanisms of signal transduction is still unclear, tyrosine kinases have been shown to be important contributing factors in cell proliferation, carcinogenesis and cell differentiation. Tyrosine kinases can be categorized as receptor type or non-receptor type. Both receptor-type and non-receptor type tyrosine kinases are implicated in cellular signaling pathways leading to numerous pathogenic conditions, including cancer, psoriasis and hyperimmune responses. Many tyrosine kinases are involved in cell growth as well as in angiogenesis. The non-receptor type of tyrosine kinases is also comprised of numerous subfamilies, including Src, Frk, Btk, Csk, Abl, Zap70, Fes/Fps, Fak, Jak, Ack, and LIMK. Each of these subfamilies is further sub-divided into varying receptors. For example, the Src subfamily is one of the largest and includes Src, Yes, Fyn, Lyn, Lck, Blk, Hck, Fgr, and Yrk. The Src subfamily of enzymes has been linked to oncogenesis. For a more detailed discussion of the non-receptor type of tyrosine kinases, see Bolen *Oncogene,* 8:2025-2031 (1993).

Receptor type tyrosine kinases have an extracellular, a transmembrane, and an intracellular portion, while non-receptor type tyrosine kinases are wholly intracellular. Receptor-linked tyrosine kinases are transmembrane proteins that contain an extracellular ligand binding domain, a transmembrane sequence, and a cytoplasmic tyrosine kinase domain. The receptor-type tyrosine kinases are comprised of a large number of transmembrane receptors with diverse biological activity.

Different subfamilies of receptor-type tyrosine kinases have been identified. Implicated tyrosine kinases include fibroblast growth factor (FGF) receptors, epidermal growth factor (EGF) receptors of the ErbB major class family, and platelet-derived growth factor (PDGF) receptors. Also implicated are nerve growth Factor (NGF) receptors, brain-derived neurotrophic Factor (BDNF) receptors, and neurotrophin-3 (NT-3) receptors, and neurotrophin-4 (NT-4) receptors.

One receptor type tyrosine kinase subfamily, designated as HER or ErbB subfamily, is comprised of EGFR (ErbB1), HER2 (ErbB2 or p185neu), HER3 (ErbB3), and HER4 (ErbB4). Ligands of this subfamily of receptors include epithelial growth factor (EGF), TGF-α, amphiregulin, HB-EGF, betacellulin, heregulin and neuregulins. The PDGF subfamily includes the FLK family which is comprised of the kinase insert domain receptor (KDR).

EGFR, encoded by the erbB1 gene, has been causally implicated in human malignancy. In particular, increased expression of EGFR has been observed in breast, bladder, lung, head, neck and stomach cancer as well as glioblastomas. Increased EGFR receptor expression is often associated with increased production of the EGFR ligand, transforming growth factor alpha (TGF-a), by the same tumor cells resulting in receptor activation by an autocrine stimulatory pathway (Baselga and Mendelsohn, *Pharmac. Ther.* 64:127-154 (1994)).

The EGF receptor is a transmembrane glycoprotein which has a molecular weight of 170.000, and is found on many epithelial cell types. It is activated by at least three ligands, EGF, TGF-α (transforming growth factor alpha) and amphiregulin. Both epidermal growth factor (EGF) and transforming growth factor-alpha (TGF-a) have been demonstrated to bind to EGF receptor and to lead to cellular proliferation and tumor growth. These growth factors do not bind to HER2 (Ulrich and Schlesinger, 1990, Cell 61, 203). In contrary to several families of growth factors, which induce receptor dimerization by virtue of their dimeric nature (e.g. PDGF) monomeric growth factors, such as EGF, contain two binding sites for their receptors and, therefore, could principally cross-link two neighboring EGF receptors (Lemmon et al., 1997, EMBO J. 16, 281). Recent studies (J. Schlessinger, 2002, Cell 110, 669) show that receptor dimerization is mediated by receptor-receptor interactions in which a loop protruding from neighboring receptors mediates receptor dimerization and activation.

Receptor dimerization is essential for stimulating of the intrinsic catalytic activity and for the self-phosphorylation of growth factor receptors on tyrosine residues. The latter serve as docking sites for various adaptor proteins or enzymes, which simultaneously initiate many signaling cascades. In higher eukaryotes, the simple linear pathway has evolved into a richly interactive, multi-layered network in which combinatorial expression and activation of components permits context-specific biological responses throughout development. The ErbB network might integrate not only its own inputs but also heterologous signals, including hormones, lymphokines, neurotransmitters and stress inducers.

It should be remarked that receptor protein tyrosine kinases (PTKs) are able to undergo both homo- and heterodimerization, wherein homodimeric receptor combinations are less mitogenic and transforming (no or weak initiation of signaling) than the corresponding heterodimeric combinations. Heterodimers containing ErbB2 are the most potent complexes (see review articles by Yarden and Sliwkowski, 2001, Nature Reviews, Molecular cell Biology, volume 2, 127-137; Tzahar and Yarden, 1998, BBA 1377, M25-M37).

It has been demonstrated that anti-EGF receptor antibodies while blocking EGF and TGF-α binding to the receptor appear to inhibit tumor cell proliferation. In view of these findings, a number of murine and rat monoclonal antibodies against EGF receptor have been developed and tested for their ability inhibit the growth of tumor cells in vitro and in vivo (Modjtahedi and Dean, 1994, J. Oncology 4, 277). Humanized monoclonal antibody 425 (hMAb 425, U.S. Pat. No. 5,558,864; EP 0531 472) and chimeric monoclonal antibody 225 (cMAb 225), both directed to the EGF receptor, have shown their efficacy in clinical trials. The C225 antibody (Cetuximab) was demonstrated to inhibit EGF-mediated tumor cell growth in vitro and to inhibit human tumor formation in vivo in nude mice. The antibody as well as in general all anti-EGFR antibodies, appears to act, above all, in synergy with certain chemotherapeutic agents (i.e., doxorubicin, adriamycin, taxol, and cisplatin) to eradicate human tumors in vivo in xenograft mouse models (see, for example, EP 0667165). Ye et al. (1999, Oncogene 18, 731) have reported that human ovarian cancer cells can be treated successfully with a combination of both chimeric MAb 225 and humanized MAb 4D5 which is directed to the HER2 receptor.

The second member of the ErbB family, HER2 (ErbB2 or p185neu), was originally identified as the product of the transforming gene from neuroblastomas of chemically treated rats. The activated form of the neu proto-oncogene results from a point mutation (valine to glutamic acid) in the transmembrane region of the encoded protein. Amplification of the human homologue of neu is observed in breast and ovarian cancers and correlates with a poor prognosis (Slamon et al., *Science,* 235: 177-182 (1987); Slamon et al., *Science,* 244:707-7 12 (1989); U.S. Pat. No. 4,968,603). ErbB2 (HER2) has a molecular weight of about 185.000, with considerable homology to the EGF receptor (HER1), although a specific ligand for HER2 has not yet been clearly identified so far. The antibody 4D5 directed to the HER2 receptor, was further found to sensitize ErbB2-overexpressing breast tumor cell lines to the cytotoxic effects of TNFα (U.S. Pat. No. 5,677,171). A recombinant humanized version of the murine anti-ErbB2 antibody 4D5 (huMAb4D5-8, rhuMAb HER2 or HERCEPTIN®; U.S. Pat. No. 5,821,337) is clinically active in patients with ErbB2-overexpressing metastatic breast cancers that have received extensive prior anti-cancer therapy (Baselga et al., *J. Clin. Oncol.* 14:737-744 (1996)). HERCEP-TIN® received marketing approval in 1998 for the treatment of patients with metastatic breast cancer whose tumors overexpress the ErbB2 protein.

Besides anti-ErbB antibodies there are numerous small chemical molecules which are known to be potent inhibitors of ErbB receptor molecules blocking the binding site of the natural ligands (see detailed description), or blocking the tyrosine residues of the binding site of the receptor kinase, thus preventing phosphorylation and further cascade signaling. One representative showing high efficacy in clinical trials is Iressa™ (ZD-1839) which can be applied for NSCLC indication (non-small cell lung cancer).

Although there are already some promising drugs and methods of treatment tumors under development and in the market, there is a continuous need for further agents and pharmaceutical compositions and combinations with improved properties and enhanced efficacy.

SUMMARY OF THE INVENTION

The invention is based on the observation of the inventors, that certain receptor tyrosine kinases such as ErbB receptor antibody molecules, preferably ErbB1 receptor (EGFR) antibody molecules, which are overexpressed on diseased cell surfaces, e.g. tumor cells, have specific epitope sites within the natural ligand binding domain to which simultaneously different antibody molecules may be bound without or only negligible mutual hindrance. Evidently, these antibody molecules possess binding epitopes which are with respect to their three-dimensional configuration relatively small, as compared with the total size of the binding domain of the receptor molecule. They induce an increased modulation activity of pathway signaling, preferably an increased blocking of the ErbB receptor and, thus, of the complete signaling cascade. The present invention describes for the first time the new concept in tumor therapy to administer to an individual one or more biologically and therapeutically effective agents that block or inhibit an ErbB receptor, preferably the EGF receptor (EGFR) (ErbB1), by binding said agent(s) to at least a first and a second different epitope, preferably within the natural ligand domain of the same receptor. It could be found that, e.g., two or more, preferably two, distinct receptor-antagonistic molecules can bind simultaneously to the same receptor domain, preferably of the same receptor molecule, without mutual hindrance or competition, thus enabling a higher density of antagonist bound to the receptor and affecting (by a less ability to bind natural (agonistic) ligands such as EGF or TGF a) a much stronger inhibition of the signaling cascade of the corresponding receptor molecules as monomeric or dimeric units. This should lead to a stronger inhibition of tumor growth and/or increased apoptosis of solid tumors or tumor metastases. Said molecules may be small chemical and synthetic compounds or proteins, polypeptides or peptides, immunoglobulins, such as antibodies or fragments thereof, or immunoconjugates. Preferred molecules are anti-ErbB antibodies, especially anti-EGFR and anti-Her2 antibodies as specified above and below, and fragments thereof, preferably F(ab')2. In a preferred embodiment of this invention two different anti-EGFR antibodies are administered to an individual, preferably MAb 425 in a humanized, chimeric or murine version or a fragment thereof, such as a F(ab')2, and MAb 225, in a humanized, chimeric or murine version or a fragment thereof, such as a F(ab')2. Most preferred is the combinatorial application of humanized MAb 425 and chimeric MAb 225 as a whole antibody or as F(ab')2 fragment.

It is however also possible to use relatively short synthetic (poly)peptides deriving and produced from said antibody constructs comprising amino acid sequences of one, two or three CDRs of the respective antibody, wherein, optionally, in order to increase the binding affinity and/or avidity to the receptor, some amino acids within the antigen binding site or in close vicinity thereof (1-5 amino acids) may be modified by preferably substitution. Such synthetic peptides which can bind to the receptor in a comparable manner as the respective antibodies have the advantage of a simple and cheaper way of manufacture. It is also possible to synthesize one single peptide that comprises said CDR-derived amino acid sequences of the first molecule as well as of the second molecule, for example a (poly)peptide comprising amino acid sequences deriving from 1-3 CDRs of MAb 425 and 1-3 CDRs of MAb 225.

It was found that the pharmaceutical compositions according to this invention can affect enhanced cross-linking/dimerization of different or identical ErbB receptors, enhanced blocking/inhibition of ErbB receptors, and enhanced induction of modulation of ErbB receptor-specific pathway signaling as compared with a single molecule comprising one of said binding sites only. In other words: a mixture of, for example, MAb 425 and MAb 225 elicit an enhanced inhibition and down-regulation of EGFR as compared to MAbs 425 or 225 applied as single agent in the same concentration.

Although above-described observations were made for ErbB receptors as target receptor molecules only it should be pointed out that the scientific principle discovered by the inventors and stated out above and below might be also applicable for other biological receptors other than ErbB.

Optionally, the composition according to this invention comprises further therapeutically active compounds which may support and enhance the efficacy of above-said molecules. Such agents may cytotoxic agents and preferably antagonistic molecules, such as tyrosine kinase antagonists, other ErbB antagonists, hormone growth receptor antagonists, protein kinase antagonists, anti-angiogenic agents, or cytokines. Such molecules usable in the present invention are specified in more detail below.

According to this invention the therapeutically active agents may also be provided by means of a pharmaceutical kit comprising a packages containing one or more of said antagonistic agents in single or separate containers. The therapy with this combinations may include optionally treatment with radiation. Principally, the administration can be accompanied by radiation therapy, wherein radiation treatment can be done substantially concurrently or before or after the drug administration. The administration of the different agents of the combination therapy according to the invention can also be achieved substantially concurrently or sequentially. Tumors, bearing receptors on their cell surfaces involved in the development of the blood vessels of the tumor, may be successfully treated by the combination therapy of this invention.

It is known that tumors elicit alternative routes for their development and growth. If one route is blocked they often have the capability to switch to another route by expressing and using other receptors and signaling pathways. Therefore, the pharmaceutical combinations of the present invention may block several of such possible development strategies of the tumor and provide consequently various benefits. The combinations according to the present invention are useful in treating and preventing tumors, tumor-like and neoplasia disorders and tumor metastases, which develop and grow by activation of their relevant hormone receptors which are present on the surface of the tumor cells. Preferably, the different combined agents of the present invention are administered in combination at a low dose, that is, at a dose lower than has been conventionally used in clinical situations. A benefit of lowering the dose of the compounds, compositions, agents and therapies of the present invention administered to an individual includes a decrease in the incidence of adverse effects associated with higher dosages. For example, by the lowering the dosage of an agent described above and below, a reduction in the frequency and the severity of nausea and vomiting will result when compared to that observed at higher dosages. By lowering the incidence of adverse effects, an improvement in the quality of life of a cancer patient is contemplated. Further benefits of lowering the incidence of adverse effects include an improvement in patient compliance, a reduction in the number of hospitalizations needed for the treatment of adverse effects, and a reduction in the administration of analgesic agents needed to treat pain associated with the adverse effects. Alternatively, the methods and combination of the present invention can also maximize the therapeutic effect at higher doses.

The combinations according to the inventions show an astonishing synergetic effect. In administering the combination of drugs real tumor shrinking and disintegration could be observed during clinical studies while no significant adverse drug reactions were detectable.

In detail the invention refers to:

A pharmaceutical composition comprising one or more biologically and/or therapeutically effective antibody molecules (or a fragment thereof) having the ability to bind to different epitopes of a binding domain of an ErbB receptor molecule, wherein said one or more antibody molecule(s) comprise(s) at least a binding site that binds to a first specific epitope of said receptor binding domain and at least another binding site that binds to a second specific epitope of the same ErbB receptor binding domain.

A corresponding pharmaceutical composition, comprising two or more antibody molecules, wherein one antibody molecule comprises at least a binding site that binds to a first specific epitope of said receptor domain and at least another antibody molecule comprises at least another binding site that binds to a second specific epitope of the same receptor binding domain.

A corresponding pharmaceutical composition, wherein at least one of said antibody molecules binds to an epitope within the receptor binding domain to which the natural ligand of the receptor binds.

A corresponding pharmaceutical composition affecting enhanced blocking and/or inhibition of ErbB receptor, and enhanced induction of modulation of ErbB receptor-specific pathway signaling as compared with a single molecule comprising one of said binding sites only.

A corresponding pharmaceutical composition, affecting enhanced induction of crosslinking and/or dimerization of different receptor molecules having the same or different specificity.

A corresponding pharmaceutical composition, wherein said ErbB receptor is EGF receptor (EGFR).

A corresponding pharmaceutical composition, comprising a first and a second monoclonal antibody or a biologically active fragment thereof, each directed to different epitopes of the EGF receptor.

A corresponding pharmaceutical composition, wherein the first antibody is murine, chimeric or humanized MAb 425.

A corresponding pharmaceutical composition, wherein the second antibody is murine, chimeric or humanized MAb 225.

A corresponding pharmaceutical composition, wherein said first antibody is humanized MAb 425 (h425) and said second antibody is chimeric MAb 225 (c225, Cetuximab).

A corresponding pharmaceutical composition, comprising additionally a cytotoxic drug.

A pharmaceutical kit comprising
(i) a first package comprising at least a first biologically active antibody molecule, or a fragment thereof, that binds to a first specific epitope of a binding domain of an ErbB receptor molecule, and (ii) a second package comprising at least a second antibody molecule, or a fragment thereof, that binds to a different second specific epitope of the binding domain of the same ErbB receptor molecule.

A corresponding pharmaceutical kit, wherein at least one of said antibody molecules binds to an epitope within the receptor binding domain to which the natural ligand of the receptor binds.

A corresponding pharmaceutical kit, wherein said first antibody molecule is murine, chimeric or humanized monoclonal antibody 425 or a biologically active fragment thereof, and said second antibody molecule is murine, chimeric or humanized monoclonal antibody 225 or a biologically active fragment thereof.

A corresponding pharmaceutical kit comprising a first package that comprises humanized MAb 425 (h425) and a second package that comprises chimeric MAb 225 (c225).

A corresponding pharmaceutical kit comprising additionally a third package comprising a further drug having the ability to increase the efficacy of the drugs provided by the first and second package.

A corresponding pharmaceutical kit, wherein said additional drug is a cytotoxic drug.

A method for treating tumor related diseases in a patient comprising administering to said patient a therapeutically effective amount of (i) at least a first antibody molecule (or a fragment thereof) that binds to a first specific epitope of a binding domain of an ErbB receptor molecule and (ii) at least a second antibody molecule that binds to a different second specific epitope of the binding region of the same ErbB receptor molecule.

A corresponding method, wherein at least one of said antibody molecules binds to an epitope within the receptor binding domain to which the natural ligand of the receptor binds.

A corresponding method, wherein said antibody molecule that binds to said epitope blocks and/or inhibits the receptor, thus inducing modulation of receptor-specific pathway signaling.

A corresponding method, wherein the binding of said antibody molecule induces crosslinking and/or dimerization of different receptor molecules having the same or different specificity.

A corresponding method, wherein said first antibody molecule is humanized monoclonal antibody 425 (h425) or a biologically active fragment thereof, and said second molecule is chimeric or monoclonal antibody 225 (c225) or a biologically active fragment thereof.

In a preferred embodiment of the invention the ErbB receptor is the EGF receptor (EGFR) and the antibodies directed to different epitopes on this receptor are anti-EGFR antibodies. Thus, the invention relates in detail to:

A pharmaceutical composition comprising a first and a second antibody molecule, or a portion thereof, having the capability to bind to different epitopes located on same or different ErbB receptor molecule types, wherein said first antibody molecule or a portion thereof, comprises binding sites that bind to a first specific epitope on the ErbB1 receptor molecule type, and said second antibody molecule comprises binding sites that bind to a second specific epitope on the same ErbB1 receptor molecule type.

A pharmaceutical composition, wherein at least said first or said second epitope on the ErbB1 receptor molecule type is located within the ErbB1 receptor binding domain.

A pharmaceutical composition, wherein said first and said second epitope on the ErbB1 receptor molecule type is located within the ErbB1 receptor binding domain.

A pharmaceutical composition, wherein said receptor binding domain is the binding domain of the natural ligand of said ErbB1 receptor molecule type.

A pharmaceutical composition, wherein the first and second antibody, or fragment thereof, binds to different epitopes within the binding domain of the natural ligand(s) of said ErbB1 receptor molecule type.

A pharmaceutical composition, wherein blocking and/or inhibition of the ErbB receptor, and induction of down-regulation of ErbB receptor-specific pathway signaling is enhanced as compared with a composition comprising a single antibody molecule which binds to said first or said second epitope on said ErbB1 receptor molecule type only.

A pharmaceutical composition, wherein the induction of cross-linking and/or dimerization of ErbB receptor molecules of the same or different specificity is enhanced as compared with a composition comprising a single antibody molecule which binds to said first or said second epitope on said ErbB1 receptor molecule type only.

A pharmaceutical composition, wherein said ErbB receptor molecules, are involved in cross-linking and/or dimerization, and are selected from ErbB1 and ErbB2 (Her-2).

A pharmaceutical composition, wherein said first and/or said second antibodies is a monospecific antibody.

A pharmaceutical composition, wherein the first antibody is murine, chimeric or humanized MAb 425.

A pharmaceutical composition, wherein the second antibody is murine, chimeric or humanized MAb 225.

A pharmaceutical composition, wherein said first antibody is humanized MAb 425 (h425) and said second antibody is chimeric MAb 225 (c225).

A pharmaceutical composition according to any of the following 12 pharmaceutical compositions, comprising additionally a cytotoxic agent:

(a) A pharmaceutical composition comprising a first and a second antibody molecule, or a portion thereof, having the capability to bind to different epitopes located on same or different ErbB receptor molecule types, wherein said first antibody molecule or a portion thereof, comprises binding sites that bind to a first specific epitope on the ErbB1 receptor molecule type, and said second antibody molecule comprises binding sites that bind to a second specific epitope on the same ErbB1 receptor molecule type.

(b) A pharmaceutical composition, wherein at least said first or said second epitope on the BrbB1 receptor molecule type is located within the ErbB1 receptor binding domain.

(c) A pharmaceutical composition, wherein said first and said second epitope on the ErbB1 receptor molecule type is located within the ErbB1 receptor binding domain.

(d) A pharmaceutical composition, wherein said receptor binding domain is the binding domain of the natural ligand of said ErbB1 receptor molecule type.

(e) A pharmaceutical composition, wherein the first and second antibody, or fragment thereof, binds to different epitopes within the binding domain of the natural ligand (s) of said ErbB1 receptor molecule type.

(f) A pharmaceutical composition, wherein blocking and/or inhibition of the ErbB receptor, and induction of down-regulation of ErbB receptor-specific pathway signaling is enhanced as compared with a composition comprising a single antibody molecule which binds to said first or said second epitope on said ErbB1 receptor molecule type only.

(g) A pharmaceutical composition, wherein the induction of cross-linking and/or dimerization of ErbB receptor molecules of the same or different specificity is enhanced as compared with a composition comprising a single antibody molecule which binds to said first or said second epitope on said ErbB1 receptor molecule type only.

(h) A pharmaceutical composition, wherein said ErbB receptor molecules, are involved in cross-linking and/or dimerization, and are selected from ErbB1 and ErbB2 (Her-2).

(i) A pharmaceutical composition, wherein said first and/or said second antibodies is a monospecific antibody.

(j) A pharmaceutical composition, wherein the first antibody is murine, chimeric or humanized MAb 425.

(k) A pharmaceutical composition, wherein the second antibody is murine, chimeric or humanized MAb 225.

(l) A pharmaceutical composition, wherein said first antibody is humanized MAb 425 (h425) and said second antibody is chimeric MAb 225 (c225).

A pharmaceutical composition, wherein said cytotoxic agent is a chemotherapeutic agent.

A pharmaceutical composition, wherein said chemotherapeutic agent is selected from any of the compounds of the group: cisplatin, doxorubicin, gemcitabine, docetaxel, paclitaxel, bleomycin.

A pharmaceutical composition, wherein said cytotoxic agent is an ErbB receptor inhibitor, a VEGF receptor inhibitor, a tyrosine kinase inhibitor, a protein kinase A inhibitor, an anti-angiogenic agent, or a cytokine.

A pharmaceutical composition, wherein said first and/or said second antibody molecule is an immunoconjugate, wherein the antibody portion is fused by its C-terminus to a biologically effective peptide, polypeptide or protein, optionally via a linker peptide.

A pharmaceutical composition, wherein the protein is a cytokine.

A pharmaceutical kit comprising (i) a first package comprising a first antibody molecule, or a portion thereof, which comprises binding sites that bind to a first specific epitope present on a ErbB1 receptor molecule, and (ii) a second package comprising a second antibody molecule which comprises binding sites that bind to a second different specific epitope on the same ErbB1 receptor molecule type.

A pharmaceutical kit, wherein at least said first or said second epitope on the ErbB1 receptor is located within the ErbB1 receptor binding domain.

A pharmaceutical kit, wherein said first and said second epitope on the ErbB1 receptor is located within the ErbB1 receptor binding domain.

A pharmaceutical kit, wherein at least one of said molecules binds to an epitope within the ErbB1 receptor binding domain to which the natural ligand of the receptor binds.

A pharmaceutical kit, wherein said first antibody molecule is murine, chimeric or humanized monoclonal antibody 425, and said second molecule is murine, chimeric or humanized monoclonal antibody 225.

A pharmaceutical kit comprising a first package that comprises humanized MAb 425 (h425) and a second package that comprises chimeric MAb 225 (c225).

A pharmaceutical kit according to any of the following 6 pharmaceutical kits comprising additionally a third package comprising a cytotoxic agent.

(a) A pharmaceutical kit comprising (i) a first package comprising a first antibody molecule, or a portion thereof, which comprises binding sites that bind to a first specific epitope present on a ErbB1 receptor molecule, and (ii) a second package comprising a second antibody molecule which comprises binding sites that bind to a second different specific epitope on the ErbB1 receptor molecule type.

(b) A pharmaceutical kit, wherein at least said first or said second epitope on the ErbB1 receptor is located within the ErbB1 receptor binding domain.

(c) A pharmaceutical kit, wherein said first and said second epitope on the ErbB1 receptor is located within the ErbB1 receptor binding domain.

(d) A pharmaceutical kit, wherein at least one of said molecules binds to an epitope within the ErbB1 receptor binding domain to which the natural ligand of the receptor binds.

(e) A pharmaceutical kit, wherein said first antibody molecule is murine, chimeric or humanized monoclonal antibody 425, and said second molecule is murine, chimeric or humanized monoclonal antibody 225.

(f) A pharmaceutical kit comprising a first package that comprises humanized MAb 425 (h425) and a second package that comprises chimeric MAb 225 (c225).

A pharmaceutical kit, wherein said cytotoxic agent is a chemotherapeutic agent.

A pharmaceutical kit, wherein said chemotherapeutic agent is selected from any of the compounds of the group: cisplatin, doxorubicin, gemcitabine, docetaxel, paclitaxel, bleomycin.

A pharmaceutical kit, wherein said cytotoxic drug is an ErbB receptor inhibitor, a VEGF receptor inhibitor, a tyrosine kinase inhibitor, a protein kinase A inhibitor, an anti-angiogenic agent, or a cytokine.

Use of a pharmaceutical composition or a pharmaceutical kit as defined above and in any of the claims, for the manufacture of a medicament to treat tumors, tumor metastases or tumor related diseases which are related to overexpression of ErbB, especially ErbB1 receptors.

DETAILED DESCRIPTION OF THE INVENTION

The invention is based on the observation that two or more distinct molecules, preferably monoclonal antibodies (MAbs) with specificities for different immunogenic structures, can bind at the same time and without hindrance to their epitopes, which may be located on the same ErbB, preferably ErbB1, receptor domain, e.g. within the ErbB (ErbB1) ligand-binding domain. Application of two or more chemical or biological molecules having the described properties, such as monospecific MAbs or combinations of antibodies directed against the same or different receptors can greatly improve the therapeutic efficacy compared to the efficacy of treatment with only one monospecific antibody:

- Two or more MAbs independently bind to different epitopes on their target receptor (e.g. EGFR).
- Due to independent binding to different receptor epitopes the amount of antibody bound per receptor and thus per cell can be increased with the same antibody dose or concentration. Under optimal conditions with saturating concentrations or doses for each antibody, the number of antibody molecules bound per receptor and per cell could be theoretically doubled when two antibodies against different epitopes are used. With every additionally applied antibody a linear increase of bound antibody protein per receptor and per cell could be attained.
- Cells with antigen densities below the threshold for antibody-dependent immune effector functions, which are not vulnerable to antibody therapies under normal conditions, present increased amounts of antibody on their surface after treatment with two or more antibodies against different epitopes of the same receptor and thus become potentially accessible for ADCC and CDC.
- Compared to the efficiency of receptor blockade obtained with only one single antibody, application of two or more monospecific antibodies with specificity for different epitopes within or near the ligand-binding domain clearly increases efficacy of receptor blockade.
- Because receptor blockade by the combination of different antibodies against the same receptor domain is more effective than receptor blockade by only one single antibody, a more effective inhibition of ligand-binding is attained, which results in a more effective inactivation of the receptor.
- This more efficient receptor inactivation results in a more effective inhibition of downstream receptor signaling and consequently in an increased impact on ligand-dependent cell functions.
- Due to the more efficient receptor blockade the dosage (or concentration) of each of the applied antibodies can be reduced without loss of efficacy. This can be of great interest when therapeutic antibodies are applied, which show dose-limiting toxicities or side effects already below the optimal therapeutic dose.
- Monospecific antibodies that react with one single epitope of a receptor will only allow formation of aggregates consisting of two receptor molecules. In contrast to this, cross-linking of receptors induced by two or more antibodies against different epitopes results in receptor-antibody complexes that contain clearly larger numbers of receptors.
- Formation of larger receptor-antibody complexes induced by application of two or more antibodies improves internalization of the receptors and thus may be more efficient for removal of receptors from the cell surface and consequent down-modulation of receptor-dependent cellular functions.
- Combinations of two or more antibodies against the same or different receptors can be used for treatment of tumors carrying appropriate receptors. EGFR positive tumors are a typical example, however application of the therapeutic principle described in this invention is not limited to this indication. Thus, a wide variety of tumors carrying other receptors, receptor families or other antigenic structures can be treated using the same principle.
- The combined treatment with two or more antibodies directed against different antigens on the same or different receptors is also applicable as combination therapy together with chemotherapeutic drugs and/or irradiation.
- The combined treatment with two or more antibodies directed against different antigens on the same or different receptors as well can be used in combination with other therapeutic principles including but not limited to treatment with hormone antagonists or hormone agonists, angiogenesis inhibitors and other treatments.

The principle of combined treatment with suitable molecules, preferably antibodies, with different specificities to antigen structures on the same or different receptors is described here exemplarily for treatment of EGFR positive tumors. However, this principle is not limited to the EGFR and can be adapted for use with any other target antigen.

If not otherwise pointed out the terms and phrases used in this invention have the meanings and definitions as given below. Moreover, these definitions and meanings describe the invention in more detail, preferred embodiments included.

A "receptor" or "receptor molecule" is a soluble or membrane bound/associated protein or glycoprotein comprising one or more domains to which a ligand binds to form a receptor-ligand complex. By binding the ligand, which may be an agonist or an antagonist the receptor is activated or inactivated and may initiate or block pathway signaling.

The term "receptor molecule type" or "ErbB (ErbB1) receptor molecule type" means a specific receptor type such as ErbB1, ErbB2, etc. but not a specific single molecule of this receptor type. If it is stated herein that the antibodies according to the invention within their combination bind to a specific ErbB receptor molecule type, this does include binding of the antibodies to the same or different molecules of the same ErbB receptor type as indicated. Thus, it is possible that the first antibody binds to a specific epitope on an individual ErbB1 receptor molecule, and the second antibody binds to another different epitope of the same individual ErbB1 receptor molecule. However, it is also possible that the second antibody binds to the same or different epitope of another individual receptor molecule of the same receptor type.

By "ligand" or "receptor ligand" is meant a natural or synthetic compound which binds a receptor molecule to form a receptor-ligand complex. The term ligand includes agonists, antagonists, and compounds with partial agonist/antagonist action.

An "agonist" or "receptor agonist" is a natural or synthetic compound which binds the receptor to form a receptor-agonist complex by activating said receptor and receptor-agonist complex, respectively, initiating a pathway signaling and further biological processes.

By "antagonist" or "receptor antagonist" is meant a natural or synthetic compound that has a biological effect opposite to that of an agonist. An antagonist binds the receptor and blocks the action of a receptor agonist by competing with the agonist for receptor. An antagonist is defined by its ability to block the actions of an agonist. A receptor antagonist may be also an antibody or an immunotherapeutically effective fragment thereof. Preferred antagonists according to the present invention are cited and discussed below.

An "ErbB receptor" is a receptor protein tyrosine kinase which belongs, as already specified above, to the ErbB receptor family and includes EGFR (ErbB1), ErbB2, ErbB3 and ErbB4 receptors and other members of this family to be identified in the future. The ErbB receptor will generally comprise an extracellular domain, which may bind an ErbB ligand; a lipophilic transmembrane domain; a conserved intracellular tyrosine kinase domain; and a carboxyl-terminal signaling domain harboring several tyrosine residues which can be phosphorylated. The ErbB receptor may be a "native sequence" ErbB receptor or an "amino acid sequence variant" thereof. Preferably the ErbB receptor is native sequence human ErbB receptor. ErbB1 refers to the gene encoding the EGFR protein product. Mostly preferred is the EGF receptor (EGFR, HER1). The expressions "ErbB1" and "HER1" and "EGFR" are used interchangeably herein and refer to human HER1 protein. The expressions "ErbB2" and "HER2" are used interchangeably herein and refer to human HER2 protein. ErbB1 receptors (EGFR) are preferred according to this invention "ErbB ligand" is a polypeptide which binds to and/or activates an ErbB receptor. ErbB ligands which bind EGFR include, for example, EGF, TGF-alpha, amphiregulin, betacellulin, HB-EGF and epiregulin, preferably EGF and TGF-alpha.

"ErbB receptor binding domain" is in the context of this invention the local region (binding sequence/loop/pocket) of the ErbB receptor to which a natural ligand or an antagonistic or agonistic drug binds. This region may comprise not only one specific binding site or epitope but two or more epitopes and binding sites, respectively. One specific binding epitope within the domain binds to one kind of antagonistic or agonistic drug or ligand. Nevertheless it is deemed, that the binding of different agents to different epitopes within or nearly adjacent the binding domain of the same receptor type generally causes by inhibition or activation a distinct and unique signaling pathway that is typical for said receptor. Moreover, it should be pointed out that the phrase "within the binding domain" used in this description and claims includes also locations in close vicinity of the real binding domain of the respective natural ligand(s).

"ErbB binding epitope or binding site" means a conformation and/or configuration of amino acids within or in close vicinity of the binding domain of an ErbB receptor to which ligands or receptor antagonists/agonists bind.

"Same ErbB/ErbB1 receptor molecule" means not necessarily the identical receptor molecule, but includes also another receptor molecule of the same type. Preferably, the term relates to an identical receptor molecule.

The term "ErbB receptor antagonist/inhibitor" refers to a biologically effective molecule, which binds and blocks or inhibits the ErbB receptor. Thus, by blocking the receptor the antagonist prevents binding of the ErbB ligand (agonist) and activation of the agonist/ligand receptor complex. ErbB antagonists may be directed to HER1 (ErbB1, EGFR), HER2 (ErbB2) and ErbB3 and ErbB4. Preferred antagonists of the invention are directed to the EGF receptor (EGFR, HER1). The ErbB receptor antagonist may be an antibody or an immunotherapeutically effective fragment thereof or non-immunobiological molecules, such as a peptide, polypeptide protein. Chemical molecules are also included, however, anti-EGFR antibodies and anti-HER2 antibodies are the preferred antagonists according to the invention.

Preferred antibodies of the invention are anti-Her1 and anti-Her2 antibodies, more preferably anti-Her1 antibodies. Preferred anti-Her1 antibodies are MAb 425, preferably humanized MAb 425 (hMAb 425, U.S. Pat. No. 5,558,864; EP 0531 472) and chimeric MAb 225 (CETUXIMAB®). Most preferred is monoclonal antibody h425, which has shown in mono-drug therapy high efficacy combined with reduced adverse and side effects. Most preferred anti-HER2 antibody is HERCEPTIN® commercialized by Genentech/Roche. Efficacious EGF receptor antagonists according to the invention may be also natural or synthetic chemical compounds. Some examples of preferred molecules of this category include organic compounds, organometallic compounds, salts of organic and organometallic compounds. Examples for chemical HER2 receptor antagonists are: styryl substituted heteroaryl compounds (U.S. Pat. No. 5,656,655); bis mono and/or bicyclic aryl heteroaryl, carbocyclic, and heterocarbocyclic compounds (U.S. Pat. No. 5,646,153); tricyclic pyrimidine compounds (U.S. Pat. No. 5,679,683); quinazoline derivatives having receptor tyrosine kinase inhibitory activity (U.S. Pat. No. 5,616,582); heteroarylethenediyl or heteroaryl-ethenediylaryl compounds (U.S. Pat. No. 5,196,446); a compound designated as 6-(2,6-dichlorophenyl)-2-(4-(2-diethyl-aminoethoxy)phenylamino)-8-methyl-8H-pyrido(2,3)-5-pyrimidin-7-one (Panek, et al., 1997, J. Pharmacol. Exp. Therap. 283,1433) inhibiting EGFR, PDGFR, and FGFR families of receptors.

The term "tyrosine kinase antagonist/inhibitor" refers according to this invention to natural or synthetic agents that are enabled to inhibit or block tyrosine kinases, receptor tyrosine kinases included. Thus, the term includes per se ErbB receptor antagonists/inhibitors as defined above. With exception of the anti-ErbB receptor antibodies mentioned above and below, more preferable tyrosine kinase antagonist agents under this definition are chemical compounds which have shown efficacy in mono-drug therapy for breast and prostate cancer. Suitable indolocarbazole-type tyrosine kinase inhibitors can be obtained using information found in documents such as U.S. Pat. Nos. 5,516,771; 5,654,427; 5,461,146; 5,650,407. U.S. Pat. Nos. 5,475,110; 5,591,855; 5,594,009 and WO 96/11933 disclose pyrrolocarbazole-type tyrosine kinase inhibitors and prostate cancer. One of the most promising anti-cancer agents in this context is gefitinib (IRESSA®, Astra Zeneca), which is reported to possess outstanding therapeutic efficacy and excellent tolerability in patients with non-small cell lung cancer (NSCLC) as well as advanced head and neck cancer.

Preferably, the dosage of the chemical tyrosine kinase inhibitors as defined above is from 1 pg/kg to 1 g/kg of body weight per day. More preferably, the dosage of tyrosine kinase inhibitors is from 0.01 mg/kg to 100 mg/kg of body weight per day.

The biological molecules according to this invention are preferably antibodies or fragments thereof or any variations of antibodies such as immunoconjugates.

In this context, the term "antibody" or "immunoglobulin" herein is used in the broadest sense and specifically covers intact monoclonal antibodies, polyclonal antibodies, multi-specific antibodies (e.g. bispecific antibodies) formed from at least two intact antibodies, and antibody fragments, so long as they exhibit the desired biological activity. The term generally includes heteroantibodies which are composed of two or more antibodies or fragments thereof of different binding specificity which are linked together.

Depending on the amino acid sequence of their constant regions, intact antibodies can be assigned to different "antibody (immunoglobulin) classes". There are five major classes of intact antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called $\alpha$, $\delta$, $\epsilon$, $\gamma$ and $\mu$ respectively. Preferred major class for antibodies according to the invention is IgG, in more detail IgG1 and IgG2.

Antibodies are usually glycoproteins having a molecular weight of about 150,000, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end. The constant domain of the light chain is aligned with the first constant domain of the heavy chain, and the light-chain variable domain is aligned with the variable domain of the heavy chain. Particular amino acid residues are believed to form an interface between the light chain and heavy chain variable domains. The "light chains" of antibodies from any vertebrate species can be assigned to one of two clearly distinct types, called kappa (κ) and lambda (λ), based on the amino acid sequences of their constant domains.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. Methods for making monoclonal antibodies include the hybridoma method described by Kohler and Milstein (1975, Nature 256, 495) and in "Monoclonal Antibody Technology, The Production and Characterization of Rodent and Human Hybridomas" (1985, Burdon et al., Eds, Laboratory Techniques in Biochemistry and Molecular Biology, Volume 13, Elsevier Science Publishers, Amsterdam), or may be made by well known recombinant DNA methods (see, e.g., U.S. Pat. No. 4,816,567). Monoclonal antibodies may also be isolated from phage antibody libraries using the techniques described in Clackson et al., Nature, 352:624-628 (1991) and Marks et al., J. Mol. Biol., 222:58, 1-597(1991), for example.

The term "chimeric antibody" means antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (e.g.: U.S. Pat. No. 4,816,567; Morrison et al., Proc. Nat. Acad. Sci. USA, 81:6851-6855 (1984)). Methods for making chimeric and humanized antibodies are also known in the art. For example, methods for making chimeric antibodies include those described in patents by Boss (Celltech) and by Cabilly (Genentech) (U.S. Pat. Nos. 4,816,397; 4,816,567).

"Humanized antibodies" are forms of non-human (e.g., rodent) chimeric antibodies that contain minimal sequence derived from non-human immunoglobulin. For the most part, humanized antibodies are human immunoglobulins (recipient antibody) in which residues from a hypervariable region (CDRs) of the recipient are replaced by residues from a hypervariable region of a non-human species (donor antibody) such as mouse, rat, rabbit or nonhuman primate having the desired specificity, affinity and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. Methods for making humanized antibodies are described, for example, by Winter (U.S. Pat. No. 5,225,539) and Boss (Celltech, U.S. Pat. No. 4,816,397).

"Antibody fragments" comprise a portion of an intact antibody, preferably comprising the antigen-binding or variable region thereof. Examples of antibody fragments include Fab, Fab', F(ab')2, Fv and Fc fragments, diabodies, linear antibodies, single-chain antibody molecules; and multispecific antibodies formed from antibody fragment(s). An "intact" antibody is one which comprises an antigen-binding variable region as well as a light chain constant domain (CL) and heavy chain constant domains, CH1, CH2 and CH3. Preferably, the intact antibody has one or more effector functions. Papain digestion of antibodies produces two identical antigen-binding fragments, called "Fab" fragments, each comprising a single antigen-binding site and a CL and a CH1 region, and a residual "Fc" fragment, whose name reflects its ability to crystallize readily.

The "Fc" region of the antibodies comprises, as a rule, a CH2, CH3 and the hinge region of an IgG1 or IgG2 antibody major class. The hinge region is a group of about 15 amino acid residues which combine the CH1 region with the CH2-CH3 region.

Pepsin treatment yields an "F(ab')2" fragment that has two antigen-binding sites and is still capable of cross-linking antigen.

"Fv" is the minimum antibody fragment which contains a complete antigen-recognition and antigen-binding site. This region consists of a dimer of one heavy chain and one light chain variable domain in tight, non-covalent association. It is in this configuration that the three hypervariable regions (CDRs) of each variable domain interact to define an antigen-binding site on the surface of the VH-VL dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The "Fab" fragment also contains the constant domain of the light chain and the first constant domain (CH1) of the heavy chain and has one antigen-binding site only. "Fab'" fragments differ from Fab fragments by the addition of a few residues at the carboxy terminus of the heavy chain CH1 domain including one or more cysteines from the antibody hinge region.

F(ab')2 antibody fragments originally were produced as pairs of Fab' fragments which have hinge cysteines between them. Other chemical couplings of antibody fragments are also known (see e.g. Hermanson, Bioconjugate Techniques, Academic Press, 1996; U.S. Pat. No. 4,342,566).

"Single-chain Fv" or "scFv" antibody fragments comprise the $V_H$ and $V_L$ domains of antibody, wherein these domains are present in a Single polypeptide chain. Preferably, the Fv polypeptide further comprises a polypeptide linker between the VH and VL domains which enables the scFv to form the desired structure for antigen binding. Single-chain FV antibodies are known, for example, from Plückthun (*The Pharmacology of Monoclonal Antibodies*, Vol. 113, Rosenburg and Moore eds., Springer-Verlag, New York, pp. 269-315 (1994)), WO93/16185; U.S. Pat. Nos. 5,571,894; 5,587,458; Huston et al. (1988, Proc. Natl. Acad. Sci. 85, 5879) or Skerra and Plueckthun (1988, Science 240, 1038).

The term "variable" or "FR" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called "hypervariable" regions both in the light chain and the heavy chain variable domains. The more highly conserved portions of variable domains are called the framework regions (FRs). The variable domains of native heavy and light chains each comprise four FRs (FR1-FR4), largely adopting a β-sheet configuration, connected by three hypervariable regions, which form loops connecting, and in some cases forming part of the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest*, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC). The term "hypervariable region" or "CDR" when used herein refers to the amino acid residues of an antibody which are responsible for antigen-binding. The hypervariable region generally comprises amino acid residues from a "complementarity determining region" or "CDR" (e.g. residues 24-34 (L1), 50-56 (L2) and 89-97 (L3) in the light chain variable domain and 31-35 (H1), 50-65 (H2) and 95-102 (H3) in the heavy chain variable domain; and/or those residues from a "hypervariable loop" (e.g. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk *J. Mol. Biol.* 196:901-917 (1987)).

"Framework Region" or "FR" residues are those variable domain residues other than the hypervariable region residues as herein defined.

The term "monospecific" refers to antibodies according to this invention, wherein the two binding sites of the antibody have the same specificity, thus, being able to bind to the same epitope on the receptor. Preferably, according to this invention, the pharmaceutical compositions comprise monospecific antibodies.

"Bispecific antibodies" (BAbs) are single, divalent antibodies (or immunotherapeutically effective fragments thereof) which have two differently specific antigen binding sites. According to this invention BAbs are characterized as BAb<MAb 1, MAb 2>, wherein <MAb 1> and <MAb 2> designates the antigen-binding sites deriving from MAb 1 and MAb 2. For example the first antigen binding site is directed to an angiogenesis receptor (e.g. integrin or VEGF receptor), whereas the second antigen binding site is directed to an ErbB receptor (e.g. EGFR or HER2). Bispecific antibodies can be produced by chemical techniques (see e.g., Kranz et al. (1981) Proc. Natl. Acad. Sci. USA 78, 5807), by "polydoma" techniques (See U.S. Pat. No. 4,474,893) or by recombinant DNA techniques, which all are known per se. Further methods are described in WO 91/00360, WO 92/05793 and WO 96/04305. Bispecific antibodies can also be prepared from single chain antibodies (see e.g., Huston et al. (1988) Proc. Natl. Acad. Sci. 85, 5879; Skerra and Plueckthun (1988) Science 240, 1038). These are analogues of antibody variable regions produced as a single polypeptide chain. To form the bispecific binding agent, the single chain antibodies may be coupled together chemically or by genetic engineering methods known in the art. It is also possible to produce bispecific antibodies according to this invention by using leucine zipper sequences. The sequences employed are derived from the leucine zipper regions of the transcription factors Fos and Jun (Landschulz et al., 1988, Science 240, 1759; for review, see Maniatis and Abel, 1989, Nature 341, 24). Leucine zippers are specific amino acid sequences about 20-40 residues long with leucine typically occurring at every seventh residue. Such zipper sequences form amphipathic α-helices, with the leucine residues lined up on the hydrophobic side for dimer formation. Peptides corresponding to the leucine zippers of the Fos and Jun proteins form heterodimers preferentially (O'Shea et al., 1989, Science 245, 646). Zipper containing bispecific antibodies and methods for making them are also disclosed in WO 92/10209 and WO 93/11162.

The term "fusion protein" refers to a natural or synthetic molecule consisting of one ore more biological molecules as defined above, wherein two or more peptide- or protein-based (glycoproteins included) molecules having different specificity are fused together optionally by chemical or amino acid based linker molecules. The linkage may be achieved by C—N fusion or N—C fusion (in 5'→3' direction), preferably C—N fusion. Preferred fusion proteins according to the invention are, however, immunoconjugates as defines below.

The term "immunoconjugate" refers to a fusion protein and means an antibody or immunoglobulin, respectively, or a immunologically effective fragment thereof, which is fused by covalent linkage to a non-immunologically effective molecule. Preferably this fusion partner is a peptide or a protein, which may be glycosylated. Said non-antibody molecule can be linked to the C-terminal of the constant heavy chains of the antibody or to the N-terminals of the variable light and/or heavy chains. The fusion partners can be linked via a linker molecule, which is, as a rule, a 3-15 amino acid residues containing peptide. Immunoconjugates according to this invention are fusion proteins consisting of an immunoglobulin or immunotherapeutically effective fragment thereof, directed to an ErbB receptor, and preferably a cytokine, such as TNFα, IFNγ or IL-2, or another toxic agent. Preferably, these peptide- or protein-based molecules are linked with their N-terminal to the C-terminal of said immunoglobulin, which is the Fc portion thereof.

"Heteroantibodies" are fusion proteins consisting essentially of two or more antibodies or antibody-binding fragments which are fused together by regularly chemical cross-linkers, each of said antibodies having a different binding specificity. Heteroantibodies can be prepared by conjugating together two or more antibodies or antibody fragments. Preferred heteroantibodies are comprised of cross-linked Fab/Fab' fragments. A variety of coupling or cross-linking agents can be used to conjugate the antibodies. Examples are protein A, carboiimide, N-succinimidyl-S-acetyl-thioacetate (SATA) and N-succinimidyl-3-(2-pyridyldithio)propionate (SPDP) (see e.g., Karpovsky et al. (1984) J. EXP. Med. 160, 1686; Liu et a. (1985) Proc. Natl. Acad. Sci. USA 82, 8648). Other methods include those described by Paulus, Behring Inst. Mitt., No. 78, 118 (1985); Brennan et al. (1985) Science 30, 81, or Glennie et al. (1987), J. Immunol. 139, 2367. Another method uses o-phenylenedimaleimide (oPDM) for coupling three Fab' fragments (WO 91/03493). Multispecific antibodies are in context of this invention also suitable and can be prepared, for example according to the teaching of WO 94/13804 and WO 98/50431. A preferred heteroantibody according to this invention is a fusion protein comprising two anti-EGFR antibodies (each antibody is directed to different epitopes of the same receptor) linked together as described (e.g. MAB 425-MAB 225).

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; mouse gonadotropin-associated peptide; inhibin; activin; vascular endothelial growth factor (VEGF); integrin; thrombopoietin (TPO); nerve growth factors such as NGF.beta.; platelet-growth factor; transforming growth factors (TGFs) such as TGF.alpha. and TGF.beta.; erythropoietin (EPO); interferons such as IFN.alpha., IFN-.beta., and IFN.gamma.; colony stimulating factors such as M-CSF, GM-CSF and G-CSF; interleukins such as IL-1, IL-1a, IL-2, IL-3, IL-4, IL-5, IL-6, IL-7, IL-8, IL-9, IL-10, IL-11, IL-12; and TNF-.alpha. or TNF-.beta.. Preferred cytokines according to the invention are interferons, TNF.alpha. and IL-2.

Antibody "effector functions" refer to those biological activities attributable to the Fc region (a native sequence Fc region or amino acid sequence variant Fc region) of an antibody. Examples of antibody effector functions include complement dependent cytotoxicity, Fc receptor binding, antibody-dependent cell-mediated cytotoxicity (ADCC), phagocytosis; down regulation of cell surface receptors (e.,g. B cell receptor), etc.

The term "ADCC" (antibody-dependent cell-mediated cytotoxicity) refers to a cell-mediated reaction in which non-specific cytotoxic cells that express Fc receptors (FcR) (e.g. natural killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. To assess ADCC activity of a molecule of interest, an in vitro ADCC assay, such as that described in the prior art (U.S. Pat. Nos. 5,500,362; 5,821, 337) may be performed. Useful effector cells for such assays include peripheral blood mononuclear cells (PBMC) and natural killer (NK) cells.

The terms "Fc receptor" or "FcR" are used to describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcRs are reviewed, for example, in Ravetch and Kinet, *Annu. Rev. Immunol* 9:457-92 (1991).

The therapeutic approach of this invention includes as a specific embodiment the administration of further therapeutically effective agents, which support the desired effect, e.g. tumor toxicity or cytostatic efficacy, or diminish or prevent undesired side effects. Thus the invention includes the combination of such agents with the pharmaceutical composition defined and claimed above and below, wherein said agents may be other ErbB receptor antagonists, VEGF receptor antagonists, cytokines, cytokine immunoconjugates, anti-angiogenic agents, anti-hormonal agents, or cytotoxic agents in general. It is also an object of this invention to combine the compositions as defined herein with radiotherapy according to known methods.

The term "cytotoxic agent" as used in this context is defined very broadly and refers to a substance that inhibits or prevents the function of cells and/or causes destruction of cells (cell death), and/or exerts anti-neoplastic/anti-proliferative effects, for example, prevents directly or indirectly the development, maturation or spread of neoplastic tumor cells. The term includes expressively also such agents that cause a cytostatic effect only and not a mere cytotoxic effect.

The term includes chemotherapeutic agents as specified below, as well as other ErbB antagonists (such as anti-ErbB antibodies), anti-angiogenic agents, tyrosine kinase inhibitors, protein kinase A inhibitors, members of the cytokine family, radioactive isotopes, and toxins such as enzymatically active toxins of bacterial, fungal, plant or animal origin.

The term "chemotherapeutic agent" is a subset of the term "cytotoxic agent" and means specifically chemical agents that exert anti-neoplastic effects, preferably directly on the tumor cell, and less indirectly through mechanisms such as biological response modification. Suitable chemotherapeutic agents according to the invention are preferably natural or synthetic chemical compounds. There are large numbers of anti-neoplastic chemical agents available in commercial use, in clinical evaluation and in pre-clinical development, which could be included in the present invention for treatment of tumors/neoplasia by combination therapy with the receptor antagonists as claimed and described in this invention. It should be pointed out that the chemotherapeutic agents can be administered optionally together with said ErbB receptor antagonists, preferably said anti-EGFR antibodies, according to the invention.

Examples of chemotherapeutic or agents include alkylating agents, for example, nitrogen mustards, ethyleneimine compounds, alkyl sulphonates and other compounds with an alkylating action such as nitrosoureas, cisplatin and dacarbazine; antimetabolites, for example, folic acid, purine or pyrimidine antagonists; mitotic inhibitors, for example, vinca alkaloids and derivatives of podophyllotoxin; cytotoxic antibiotics and camptothecin derivatives.

Preferred chemotherapeutic agents are amifostine (ethyol), cisplatin, dacarbazine (DTIC), dactinomycin, mechlorethamine (nitrogen mustard), streptozocin, cyclophosphamide, carrnustine (BCNU), lomustine (CCNU), doxorubicin (adriamycin), doxorubicin lipo (doxil), gemcitabine (gemzar), daunorubicin, daunorubicin lipo (daunoxome), procarbazine, mitomycin, cytarabine, etoposide, methotrexate, 5-fluorouracil (5-FU), vinblastine, vincristine, bleomycin, paclitaxel (taxol), docetaxel (taxotere), aldesleukin, asparaginase, busulfan, carboplatin, cladribine, camptothecin, CPT-11, 10-hydroxy-7-ethyl-camptothecin (SN38), gefitinib (Iressa), dacarbazine, floxuridine, fludarabine, hydroxyurea, ifosfamide, idarubicin, mesna, interferon alpha, interferon beta, irinotecan, mitoxantrone, topotecan, leuprolide, megestrol, melphalan, mercaptopurine, plicamycin, mitotane, pegaspargase, pentostatin, pipobroman, plicamycin, streptozocin, tamoxifen, teniposide, testolactone, thioguanine, thiotepa, uracil mustard, vinorelbine, chlorambucil and combinations thereof.

Most preferred chemotherapeutic agents according to the invention are cisplatin, gemcitabine, doxorubicin, paclitaxel (taxol) and bleomycin.

An "anti-angiogenic agent" refers to a natural or synthetic compound which blocks, or interferes with to some degree, the development of blood vessels. The anti-angiogenic molecule may, for instance, be a biological molecule that binds to and blocks an angiogenic growth factor or growth factor receptor. The preferred anti-angiogenic molecule herein binds to an receptor, preferably to an integrin receptor or to VEGF receptor. The term includes according to the invention also a prodrug of said angiogenic agent. The term furthermore includes agents effective as described and also classified as cytotoxic, preferably, chemotherapeutic agents.

There are a lot of molecules having different structure and origin which elicit anti-agiogenic properties. Most relevant classes of angiogenesis inhibiting or blocking agents which are suitable in this invention, are, for example:

(i) anti-mitotics such as flurouracil, mytomycin-C, taxol;
(ii) estrogen metabolites such as 2-methoxyestradiol;
(iii) matrix metalloproteinase (MMP) inhibitors, which inhibit zinc metalloproteinases metalloproteases) (e.g. betimastat, BB16, TIMPs, minocycline, GM6001, or those described in "Inhibition of Matrix Metalloproteinases: Therapeutic Applications" (Golub, Annals of the New York Academy of Science, Vol. 878a; Greenwald, Zucker (Eds.), 1999);
(iv) anti-angiogenic multi-functional agents and factors such as IFNα (U.S. Pat. Nos. 4,530,901; 4,503,035; 5,231,176); angiostatin and plasminogen fragments (e.g. kringle 1-4, kringle 5, kringle 1-3 (O'Reilly, M. S. et al., Cell (Cambridge, Mass.) 79(2): 315-328, 1994; Cao et al., J. Biol. Chem. 271: 29461-29467, 1996; Cao et al., J. Biol. Chem 272: 22924-22928, 1997); endostatin (O'Reilly, M. S. et al., Cell 88(2), 277, 1997 and WO 97/15666), thrombospondin (TSP-1; Frazier, 1991, Curr Opin Cell Biol 3(5): 792); platelet factor 4 (PF4);
(v) plasminogen activator/urokinase inhibitors;
(vi) urokinase receptor antagonists;
(vii) heparinases;
(viii) fumagillin analogs such as TNP-470;
(ix) tyrosine kinase inhibitors such as SU1 0. Many of the above and below mentioned ErbB receptor antagonists (EGFR/HER2 antagonists) are also tyrosine kinase inhibitors, and may show, therefore anti-EGF receptor blocking activity which results in inhibiting tumor growth, as well as anti-angiogenic activity which results in inhibiting the development of blood vessels and endothelial cells, respectively;
(x) suramin and suramin analogs;
(xi) angiostatic steroids;
(xii) VEGF and bFGF antagonists;
(xiii) VEGF receptor antagonists such as anti-VEGF receptor antibodies (DC-101);
(xiv) flk-1 and flt-1 antagonists;
(xv) cyclooxxygenase-II inhibitors such as COX-II;
(xvi) integrin antagonists and integrin receptor antagonists such as αv antagonists and αv receptor antagonists, for example, anti-αv receptor antibodies and RGD peptides. Integrin (receptor) antagonists are preferred according to this invention. The term "integrin antagonists/inhibitors" or "integrin receptor antagonists/inhibitors" refers to a natural or synthetic molecule that blocks and inhibit an integrin receptor. In some cases, the term includes antagonists directed to the ligands of said integrin receptors (such as for $\alpha_v\beta_3$: vitronectin, fibrin, fibrinogen, von Willebrand's factor, thrombospondin, laminin; for $\alpha_v\beta_5$: vitronectin; for $\alpha_v\beta_1$: fibronectin and vitronectin; for $\alpha_v\beta_6$: fibronectin).

Antagonists directed to the integrin receptors are preferred according to the invention. Integrin (receptor) antagonists may be natural or synthetic peptides, non-peptides, peptido-mimetica, immunoglobulins, such as antibodies or functional fragments thereof, or immunoconjugates (fusion proteins).

Preferred integrin inhibitors of the invention are directed to receptor of $\alpha_v$ integrins (e.g. $\alpha_v\beta_3$, $\alpha_v\beta_5$, $\alpha_v\beta_6$ and subclasses). Preferred integrin inhibitors are $\alpha_v$ antagonists, and in particular $\alpha_v\beta_3$ antagonists. Preferred $\alpha_v$ antagonists according to the invention are RGD peptides, peptidomimetic (non-peptide) antagonists and anti-integrin receptor antibodies such as antibodies blocking $\alpha_v$ receptors. Exemplary, non-immunological $\alpha_{v\beta3}$ antagonists are described in the teachings of U.S. Pat. Nos. 5,753,230 and 5,766,591. Preferred antagonists are linear and cyclic RGD-containing peptides. Cyclic peptides are, as a rule, more stable and elicit an enhanced serum half-life. The most preferred integrin antagonist of the invention is, however, cyclo-(Arg-Gly-Asp-DPhe-NMeVal) (EMD 121974, Cilengitide®, Merck KgaA, Germany; EP 0770 622) which is efficacious in blocking the integrin receptors $\alpha_v\beta_3$, $\alpha_v\beta_1$, $\alpha_v\beta_6$, $\alpha_v\beta_8$, $\alpha_{IIb}\beta_3$.

Suitable peptidic as well as peptido-mimetic (non-peptide) antagonists of the $\alpha_v\beta_3/\alpha_v\beta_5/\alpha_v\beta_6$ integrin receptor have been described both in the scientific and patent literature. For example, reference is made to Hoekstra and Poulter, 1998, Curr. Med. Chem. 5, 195; WO 95/32710; WO 95/37655; WO 97/01540; WO 97/37655; WO 97/45137; WO 97/41844; WO 98/08840; WO 98/18460; WO 98/18461; WO 98/25892; WO 98/31359; WO 98/30542; WO 99/15506; WO 99/15507; WO 99/31061; WO 00/06169; EP 0853 084; EP 0854 140; EP 0854 145; U.S. Pat. Nos. 5,780,426; and 6,048,861. Patents that disclose benzazepine, as well as related benzodiazepine and benzocycloheptene $\alpha_{v\beta3}$ integrin receptor antagonists, which are also suitable for the use in this invention, include WO 96/00574, WO 96/00730, WO 96/06087, WO 96/26190, WO 97/24119, WO 97/24122, WO 97/24124, WO 98/15278, WO 99/05107, WO 99/06049, WO 99/15170, WO 99/15178, WO 97/34865, WO 97/01540, WO 98/30542, WO 99/11626, and WO 99/15508. Other integrin receptor antagonists featuring backbone conformational ring constraints have been described in WO 98/08840; WO 99/30709; WO 99/30713; WO 99/31099; WO 00/09503; U.S. Pat. No. 5,919,792; U.S. Pat. No. 5,925,655; U.S. Pat. No. 5,981,546; and U.S. Pat. No. 6,017,926. In U.S. Pat. No. 6,048,861 and WO 00/72801 a series of nonanoic acid derivatives which are potent $\alpha_v\beta_3$ integrin receptor antagonists were disclosed. Other chemical small molecule integrin antagonists (mostly vitronectin antagonists) are described in WO 00/38665. Other $\alpha_v\beta_3$ receptor antagonists have been shown to be effective in inhibiting angiogenesis. For example, synthetic receptor antagonists such as (S)-10,11-Dihydro-3-[3-(pyridin-2-ylamino)-1-propyloxy]-5H-dibenzo[a,d]cycloheptene-10-acetic acid (known as SB-265123) have been tested in a variety of mammalian model systems. (Keenan et al., 1998, Bioorg. Med. Chem. Lett. 8(22), 3171; Ward et al., 1999, Drug Metab. Dispos. 27(11),1232). Assays for the identification of integrin antagonists suitable for use as an antagonist are described, e.g. by Smith et al., 1990, J. Biol. Chem. 265, 12267, and in the referenced patent literature. Anti-integrin receptor antibodies are also well known. Suitable anti-integrin (e.g. $\alpha_v\beta_3$, $\alpha_v\beta_5$, $\alpha_v\beta_6$) monoclonal antibodies can be modified to encompasses antigen binding fragments thereof, including F(ab)$_2$, Fab, and engineered Fv or single-chain antibody. One suitable and preferably used monoclonal antibody directed against integrin receptor $\alpha_v\beta_3$ is identified as LM609 (Brooks et al., 1994, Cell 79, 1157; ATCC HB 9537). A potent specific anti-$\alpha_v\beta_5$ antibody, P1F6, is disclosed in WO 97/45447, which is also preferred according to this invention. A further suitable $\alpha_v\beta_6$ selective antibody is MAb 14D9.F8 (WO 99/37683, DSM ACC2331, Merck KGaA, Germany) as well as MAb 17.E6 (EP 0719 859, DSM ACC2160, Merck KGaA) which is selectively directed to the $\alpha_v$- chain of integrin receptors. Another suitable anti-integrin antibody is the commercialized Vitraxin®.

As used herein, the term "anti-hormonal agent" includes natural or synthetic organic or peptidic compounds that act to regulate or inhibit hormone action on tumors. In more detail an "anti-hormonal agent" (1) inhibits the production of serum androgens, (2) blocks binding of serum androgens to androgen receptors, or (3) inhibits the conversion of testosterone to DHT, or a combination of two or more such compounds. An anti-hormonal agent according to the invention includes in general steroid receptor antagonists and in more detail anti-estrogens including for example tamoxifen, raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; and pharmaceutically acceptable salts, acids or derivatives of any of the above. The term includes also agonists and/or antagonists of glycoprotein hormones such as follicle stimulating hormone (FSH), thyroid stimulating hormone (TSH), and luteinizing hormone (LH) and LHRH (leuteinizing hormone-releasing hormone). A LHRH agonist useful in this invention is goserelin acetate, commercially available as ZOLADEX© (Zeneca). Another example of a useful LHRH antagonist is GANIRELIX© (Roche/Akzo Nobel). Examples of steroidal anti-androgens are cyproterone acetate (CPA) and megestrol acetate, commercially available as MEGACE® (Bristol-Myers Oncology). Steroidal anti-androgens may block prostatic androgen receptors. They may also inhibit the release of LH. CPA is preferably administered to human patients at dosages of 100 mg/day to 250 mg/day. Nonsteroidal anti-androgens block androgen receptors. They may also cause an increase in serum LH levels and Serum testosterone levels. A preferred nonsteroidal anti-androgen is flutamide (2-methyl-N-[4-20 nitro-3-(trifluoromethyl)phenyl] propanamide), commercially available as EULEXIN® (Schering Corp.). Flutamide exerts is anti-androgenic action by inhibiting androgen uptake, by inhibiting nuclear binding of androgen in target tissues, or both. Another non-steroidal anti-androgen is nilutamide, whose chemical name is 5,5-dimethyl-3-[4-nitro-3-(trifluoromethyl-4'-nitrophenyl)-4,4-dimethyl-imidazolidine-dione. In some embodiments of the invention, the anti-hormonal agent is a combination of an LHRH agonist such as leuprolide acetate, and an antiandrogen such as flutamide or nilutamide. For example, leuprolide acetate can be administered by subcucaneous, intramuscular or intravenous injection, and concurrently the flutamide can be administered orally. Anti-hormonal agents according to the invention include, as pointed out above, antagonists of the steroid/thyroid hormone receptors, including antagonists for other non-permissive receptors, such as antagonists for RAR, TR, VDR, and the like. As readily recognized by those of skill in the art, a variety of retinoic acid receptor (RAR) antagonists, both synthetic and naturally occurring, can be used in accordance with the present invention.

In summary, the pharmaceutical compositions and kits according to the present invention preferably can comprise the following drug combinations:
 (i) Two different monoclonal antibodies (MAb), fragments or immunoconjugates (preferably immunocytokines) thereof, directed to different epitopes of the EGF receptor.
 (ii) MAb 425 and MAb 225 or fragments or immunoconjugates (preferably immunocytokines) thereof, each directed to different epitopes of the EGF receptor.
 (iii) Humanized MAb 425 and chimeric 225 or fragments or immunoconjugates (preferably immunocytokines) thereof, each directed to different epitopes of the EGF receptor.
 (iv) (i) to (iii) in combination with one or more cytotoxic agents.
 (v) (i) to (iii), especially MAb 425 and MAb 225 in murine, chimeric or humanized versions or fragments or immunoconjugates (preferably immunocytokines) thereof, in combination with one or more chemotherapeutic agents, preferably cisplatin, gemcitabine or taxol.
 (vi) (i) to (iii), especially MAb 425 and MAb 225 in murine, chimeric or humanized versions or fragments or immunoconjugates (preferably immunocytokines) thereof, in combination with another ErbB antagonist.
 (vii) (i) to (iii), especially MAb 425 and MAb 225 in murine, chimeric or humanized versions or fragments or immunoconjugates (preferably immunocytokines) thereof, in combination with an antibody directed to ErbB-2, preferably Herceptin®, or ErbB-3, ErbB-4.
 (viii) (i) to (iii), especially MAb 425 and MAb 225 in murine, chimeric or humanized versions or fragments or immunoconjugates (preferably immunocytokines) thereof, in combination with drugs selected from the following group:
  tyrosine kinase inhibitors, such as Iressa®;
  anti-angiogenic agents, preferably integrin inhibitors, more preferably RGD peptides, cyclic peptides included, such as cyclo-(Arg-Gly-Asp-DPhe-NMe-Val) (Cilengitide®, Merck KGaA);
  anti-VEGF receptor antibodies, such as DC-101, or VEGF antagonists;
  COX-II inhibitors;
  cytokines, such as TNF-$\alpha$, IFN-$\alpha$, IFN-$\beta$, IFN-$\gamma$, IL-2;
  type I protein kinase A (PKAI) inhibitors, such as mixed backbone antisense oligonucleotides, like HYB 165 (see, for example, Tortora et al., 1999, Clin. Cancer Res., 875-881);
  anti-hormonal agents, such as goserelin, boserelin, leuprorelin, tamoxifen.

The terms "cancer" and "tumor" refer to or describe the physiological condition in mammals that is typically characterized by unregulated cell growth. By means of the pharmaceutical compositions according of the present invention tumors can be treated such as tumors of the breast, heart, lung, small intestine, colon, spleen, kidney, bladder, head and neck, ovary, prostate, brain, pancreas, skin, bone, bone marrow, blood, thymus, uterus, testicles, cervix, and liver. More specifically the tumor is selected from the group consisting of adenoma, angio-sarcoma, astrocytoma, epithelial carcinoma, germinoma, glioblastoma, glioma, hamartoma, hemangioendothelioma, hemangiosarcoma, hematoma, hepato-blastoma, leukemia, lymphoma, medulloblastoma, melanoma, neuroblastoma, osteosarcoma, retinoblastoma, rhabdomyosarcoma, sarcoma and teratoma. In detail, the tumor is selected from the group consisting of acral lentiginous melanoma, actinic keratoses, adenocarcinoma, adenoid cycstic carcinoma, adenomas, adenosarcoma, adenosquamous carcinoma, astrocytic tumors, bartholin gland carcinoma, basal cell carcinoma, bronchial gland carcinomas, capillary, carcinoids, carcinoma, carcinosarcoma, cavernous, cholangiocarcinoma, chondosarcoma, choriod plexus papilloma/carcinoma, clear cell carcinoma, cystadenoma, endodermal sinus tumor, endometrial hyperplasia, endometrial stromal sarcoma, endometrioid adenocarcinoma, ependymal, epitheloid, Ewing's sarcoma, fibrolamellar, focal nodular hyperplasia, gastrinoma, germ cell tumors, glioblastoma, glucagonoma, hemangiblastomas, hemangioendothelioma, hemangiomas, hepatic adenoma, hepatic adenomatosis, hepatocellular carcinoma, insulinoma, intraepithelial neoplasia, interepithelial squamous cell neoplasia, invasive squamous cell carcinoma, large cell carcinoma, leiomyosarcoma, lentigo maligna melanomas, malignant melanoma, malignant mesothelial tumors, medulloblastoma, medulloepithelioma, melanoma, meningeal, mesothelial, metastatic carcinoma, mucoepidermoid carcinoma, neuroblastoma, neuroepithelial adenocarcinoma nodular melanoma, oat cell carcinoma, oligodendroglial, osteosarcoma, pancreatic polypeptide, papillary serous adeno-carcinoma, pineal cell, pituitary tumors, plasmacytoma, pseudo-sarcoma, pulmonary blastoma, renal cell carcinoma, retinoblastoma, rhabdomyo-sarcoma, sarcoma, serous carcinoma, small cell carcinoma, soft tissue carcinomas, somatostatin-secreting tumor, squamous carcinoma, squamous cell carcinoma, submesothelial, superficial spreading melanoma, undifferentiated carcinoma, uveal melanoma, vermucous carcinoma, vipoma, well differentiated carcinoma, and Wilm's tumor.

Tumors which can be preferably be treated with the antibody molecules according to the invention are solid tumors or tumor metastases that express ErbB receptors, especially ErbB1 receptors, in high amounts, such as breast cancer, prostate cancer head and neck cancer, SCLC, pancreas cancer.

The term "biologically/functionally effective" or "therapeutically effective (amount)" refers to a drug/molecule which causes a biological function or a change of a biological function in vivo or in vitro, and which is effective in a specific amount to treat a disease or disorder in a mammal, preferably in a human. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can, for example, be measured by assessing the time to disease progression (TTP) and/or determining the response rate (RR).

The term "immunotherapeutically effective" refers to biological molecules which cause an immune response in a mammal. More specifically, the term refers to molecules which may recognize and bind an antigen. Typically, antibodies, antibody fragments and antibody fusion proteins comprising their antigen binding sites (complementary determining regions, CDRs) are immunotherapeutically effective.

"Radiotherapy": According to the invention the tumors can additionally be treated with radiation or radiopharmaceuticals. The source of radiation can be either external or internal to the patient being treated. When the source is external to the patient, the therapy is known as external beam radiation therapy (EBRT). When the source of radiation is internal to the patient, the treatment is called brachytherapy (BT). Some typical radioactive atoms that have been used include radium, cesium-137, and iridium-192, americium-241 and gold-198, Cobalt-57; Copper-67; Technetium-99; Iodide-123; Iodide-131; and Indium-111. It is also possible to label the agents according to the invention with radioactive isotopes. Today radiation therapy is the standard treatment to control unresectable or inoperable tumors and/or tumor metastases. Improved results have been seen when radiation therapy has been combined with chemotherapy. Radiation therapy is based on the principle that high-dose radiation delivered to a target area will result in the death of reproductive cells in both tumor and normal tissues. The radiation dosage regimen is generally defined in terms of radiation absorbed dose (rad), time and fractionation, and must be carefully defined by the oncologist. The amount of radiation a patient receives will depend on various consideration but the two most important considerations are the location of the tumor in relation to other critical structures or organs of the body, and the extent to which the tumor has spread. A preferred course of treatment for a patient undergoing radiation therapy will be a treatment schedule over a 5 to 6 week period, with a total dose of 50 to 60 Gy administered to the patient in a single daily fraction of 1.8 to 2.0 Gy, 5 days a week. A Gy is an abbreviation for Gray and refers to a dose of 100 rad. If tumors are treated with the anti-ErbB antibodies as described in this invention in context with a radiation regimen, usually a positive and even synergistic effect can be observed. In other words, the inhibition of tumor growth by means of said compounds is enhanced when combined with radiation and/or chemotherapeutic agents. Radiation therapy can be optionally used according to the invention. It is recommended and preferred in cases in which no sufficient amounts of the agents according to the invention can be administered to the patient.

"Pharmaceutical treatment": The method of the invention comprises a variety of modalities for practicing the invention in terms of the steps. For example, the agents according to the invention can be administered simultaneously, sequentially, or separately. Furthermore, the agents can be separately administered within a time interval of about 3 weeks between administrations, i.e., from substantially immediately after the first active agent is administered to up to about 3 weeks after the first agent is administered. The method can be practiced following a surgical procedure. Alternatively, the surgical procedure can be practiced during the interval between administration of the first active agent and the second active agent. Exemplary of this method is the combination of the present method with surgical tumor removal. Treatment according to the method will typically comprise administration of the therapeutic compositions in one or more cycles of administration. For example, where a simultaneous administration is practiced, a therapeutic composition comprising both agents is administered over a time period of from about 2 days to about 3 weeks in a single cycle. Thereafter, the treatment cycle can be repeated as needed according to the judgment of the practicing physician. Similarly, where a sequential application is contemplated, the administration time for each individual therapeutic will be adjusted to typically cover the same time period. The interval between cycles can vary from about zero to 2 months.

The agents of this invention can be administered parenterally by injection or by gradual infusion over time. Although the tissue to be treated can typically be accessed in the body by systemic administration and therefore most often treated by intravenous administration of therapeutic compositions, other tissues and delivery means are contemplated where there is a likelihood that the tissue targeted contains the target molecule. Thus, the agents of this invention can be administered intraocularly, intravenously, intraperitoneally, intramuscularly, subcutaneously, intracavity, transdermally, by orthotopic injection and infusion, and can also be delivered by peristaltic means. The therapeutic compositions containing, for example, an integrin antagonist of this invention are conventionally administered intravenously, as by injection of a unit dose, for example. Therapeutic compositions of the present invention contain a physiologically tolerable carrier together with the relevant agent as described herein, dissolved or dispersed therein as an active ingredient.

As used herein, the term "pharmaceutically acceptable" refers to compositions, carriers, diluents and reagents which represent materials that are capable of administration to or upon a mammal without the production of undesirable physiological effects such as nausea, dizziness, gastric upset and the like. The preparation of a pharmacological composition that contains active ingredients dissolved or dispersed therein is well understood in the art and need not be limited based on formulation. Typically, such compositions are prepared as injectables either as liquid solutions or suspensions, however, solid forms suitable for solution, or suspensions, in liquid prior to use can also be prepared. The preparation can also be emulsified. The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Particularly preferred is the HCl salt when used in the preparation of cyclic polypeptide αv antagonists. Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin. vegetable oils such as cottonseed oil, and water-oil emulsions.

Typically, a therapeutically effective amount of an immunotherapeutic agent, for example, in the form of an ErbB (ErbB1) receptor blocking antibody, an integrin receptor blocking antibody or antibody fragment or antibody conjugate or an anti-VEGF receptor blocking antibody, fragment or conjugate is an amount such that, when administered in physiologically tolerable composition, is sufficient to achieve a plasma concentration of from about 0.01 microgram (μg) per milliliter (ml) to about 100 μg/ml, preferably from about 1 μg/ml to about 5 μg/ml and usually about 5 μg/ml. Stated differently. the dosage can vary from about 0.1 mg/kg to about 300 mg/kg, preferably from about 0.2 mg/kg to about 200 mg/kg, most preferably from about 0.5 mg/kg to about 20 mg/kg, in one or more dose administrations daily for one or several days. Where the immunotherapeutic agent is in the form of a fragment of a monoclonal antibody or a conjugate, the amount can readily be adjusted based on the mass of the fragment/conjugate relative to the mass of the whole antibody. A preferred plasma concentration in molarity is from about 2 micromolar (μM) to about 5 millimolar (mM) and preferably, about 100 μM to 1 mM antibody antagonist.

A therapeutically effective amount of an agent according of this invention which is a non-immunotherapeutic peptide or a protein polypeptide or other similarly-sized biological molecule, is typically an amount of polypeptide such that when administered in a physiologically tolerable composition is sufficient to achieve a plasma concentration of from about 0.1 microgram (μg) per milliliter (ml) to about 200 μg/ml, preferably from about 1 μg/ml to about 150 μg/ml. Based on a polypeptide having a mass of about 500 grams per mole, the preferred plasma concentration in molarity is from about 2 micromolar (μM) to about 5 millimolar (mM) and preferably about 100 μM to 1 mM polypeptide antagonist.

The typical dosage of an active agent, which is a preferably a chemical cytotoxic or chemotherapeutic agent according to the invention (neither an immunotherapeutic agent nor a non-immunotherapeutic peptide/protein) is 10 mg to 1000 mg, preferably about 20 to 200 mg, and more preferably 50 to 100 mg per kilogram body weight per day. The pharmaceutical compositions of the invention can comprise phrase encompasses treatment of a subject with agents that reduce or avoid side effects associated with the combination therapy of the present invention ("adjunctive therapy"), including, but not limited to, those agents, for example, that reduce the toxic effect of anticancer drugs, e.g., bone resorption inhibitors, cardioprotective agents. Said adjunctive agents prevent or reduce the incidence of nausea and vomiting associated with chemotherapy, radiotherapy or operation, or reduce the incidence of infection associated with the administration of myelosuppressive anticancer drugs. Adjunctive agents are well known in the art. The immunotherapeutic agents according to the invention can additionally administered with adjuvants like BCG and immune system stimulators. Furthermore, the compositions may include immunotherapeutic agents or chemotherapeutic agents which contain cytotoxic effective radio-labeled isotopes, or other cytotoxic agents, such as a cytotoxic peptides (e.g. cytokines) or cytotoxic drugs and the like.

The term "pharmaceutical kit" for treating tumors or tumor metastases refers to a package and, as a rule, instructions for using the reagents in methods to treat tumors and tumor metastases. A reagent in a kit of this invention is typically formulated as a therapeutic composition as described herein, and therefore can be in any of a variety of forms suitable for distribution in a kit. Such forms can include a liquid, powder, tablet, suspension and the like formulation for providing the pharmaceutical molecules of this invention, preferably the anti-ErbB1 antibodies. The reagents may be provided in separate containers suitable for administration separately according to the present methods, or alternatively may be provided combined in a composition in a single container in the package. The package may contain an amount sufficient for one or more dosages of reagents according to the treatment methods described herein. A kit of this invention also contains "instructions for use" of the materials contained in the package.

SHORT DESCRIPTION OF THE FIGURES

FIG. 1 describes the binding of MAb 425 (EMD 72000) and c225 (Cetuximab) to different cancer cells (A431, SK-OV3, HCT 116, MiaPaca-2, KYSE-30, KYSE-70) alone and in combination, measured by flow cytometry.

EXAMPLES

Example 1

Increased Antibody Binding on a Per Cell Basis by Combining Two EGFR-Blocking Antibodies (Cetuximab, EMD 72 000) With Different Epitope Specificities.

Figure 1:
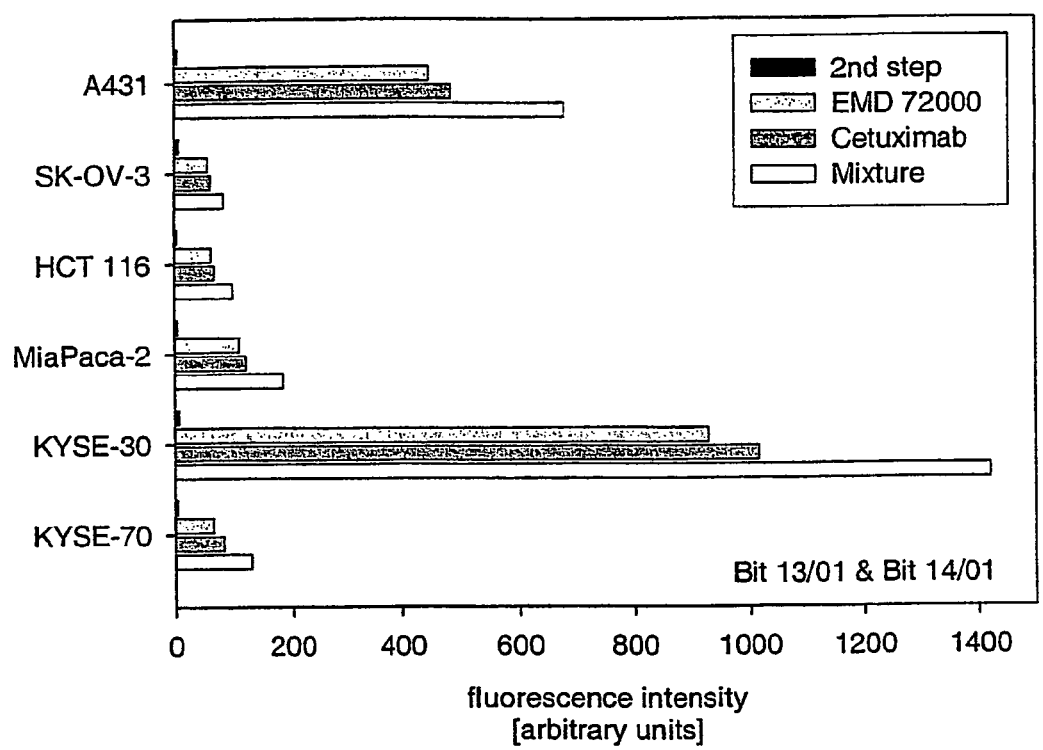

Six EGFR positive human tumor cell lines originating from epidermoid carcinoma of the vulva (A431), adenocarcinoma of the ovary (SK-OV-3), colon carcinoma (HCT 116), pancreas carcinoma (MiaPaca-2) and esophagus carcinoma (KYSE-30, KYSE-70) expressing different EGFR levels were incubated for 15 minutes on ice with 10 µg/ml Cetuximab or EMD 72 000, respectively, or with a mixture containing finally 2.5 µg/ml Cetuximab and 2.5 µg/ml EMD 72 000 (total MAb concentration: 5 µg/ml). Thereafter cells were washed and incubated for additional 15 minutes on ice with 20 µg/ml FITC labeled goat anti-human IgG+IgM(H+L)-F(ab')$_2$ as 2nd step reagent. After washing cells were analyzed by flow cytometry (FACScan. Becton Dickinson) for their fluorescence intensities, which are roughly equivalent to the amount of antibody bound per cell. As shown, independent of the reduced staining concentration used for the antibody mixture, fluorescence intensities of cells stained with this mixture were in all cases greater than fluorescence intensities of cells that were stained only with one of both antibodies at a higher concentration (FIG. 1).

Example 2

Effector-Target Cell Aggregation as Prerequisite for Antibody-Dependent Cell-Mediated Cytotoxicity and its Improvement by Combination of Two Antibodies with Specificity for Different Epitopes of the Human EGFR (Cetuximab and EMD 72 000).

In this model experiment EGFR positive A431 cells were used as target cells. EGFR negative, Fc-gamma receptor (CD64 (FcγRI) and CD32 (FcγRII)) positive U937 histiocytic lymphoma cells were used to mimic effector cells. A431 cells were fluorescence labeled with the green PKH2, U937 cells with red PKH26. Thereafter both cell lines were mixed with an effector-target cell ratio of 3:1 and incubated for 15 minutes on ice with serial dilutions (final concentrations: 4.74–0.0015 µg/ml=$3.16\times10^{-8}$–$1\times10^{-11}$ M as calculated with a MW of 150 kDa for both antibodies) Cetuximab and EMD 72 000, respectively, or with a serial dilution of a mixture of both antibodies containing half the total immunoglobulin concentration (2.37–0.00075 µg/ml=$1.58\times10^{-8}$–$5\times10^{-12}$ M; the concentration of each of the MAbs in this mixture were ½ of this concentration). After centrifugation for 5 minutes at 50×g and 4° C. cells were incubated for further 60 minutes on ice without destroying the pellets. Finally pellets were carefully resuspended and proportions of aggregates determined by flow cytometry using a FACScan instrument.

Figure 2:
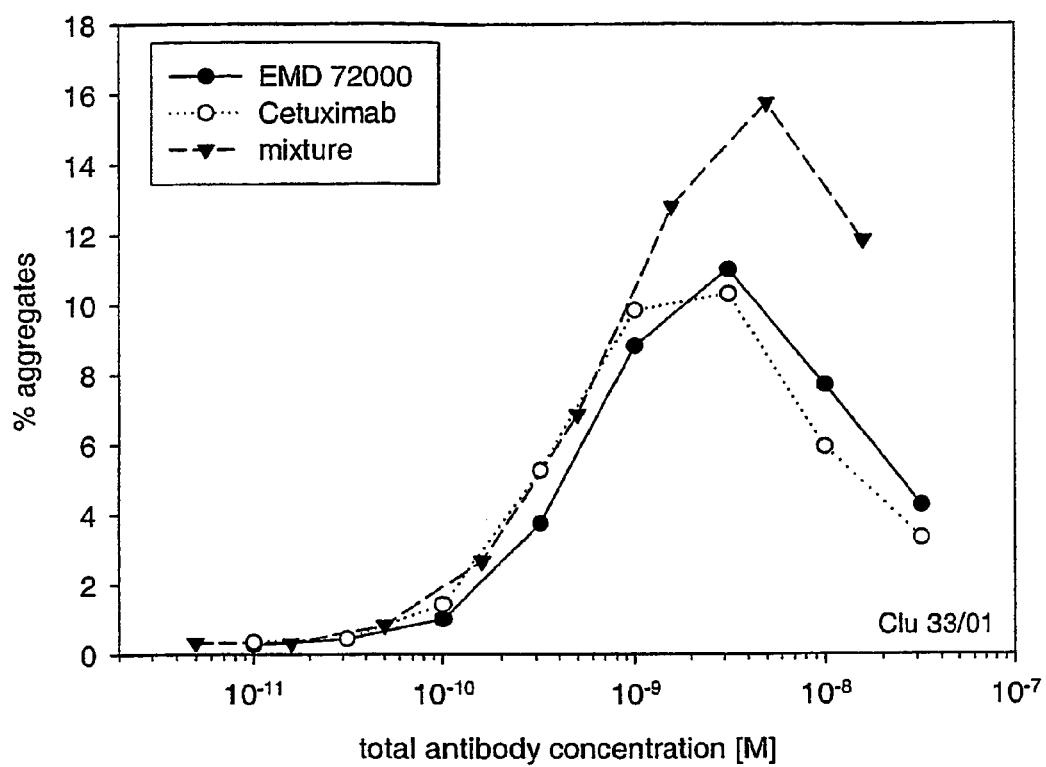
FIG. 2 depicts effector target cell aggregation in dependency on the antibody concentration (MAb 425, MAb 225, or a mixture of both).

As shown in FIG. 2, compared to results from incubation of cells with only one single antibody, the maximum percentage of aggregates is increased in samples, which were incubated with a mixture of both MAbs at a lower total protein concentration. The increasing part of the titration curve for the antibody mixture is not significantly displaced despite of the reduced protein concentration in these samples compared to samples incubated with only one of the MAbs.

Example 3

Enhanced Inhibition of EGF Binding to A431 Tumor Cells by a Mixture of Two Antibodies Directed Against Different Epitopes of the EGFR Ligand-Binding Domain.

A431 cells were preincubated for 15 minutes on ice with 0.5 µg/ml EMD 72 000, Cetuximab or a mixture of both antibodies at the same concentration. After washing off unbound antibody cells were incubated for another 15 minutes on ice with 0.01, 0.1, 1 or 10 µg/ml FITC-labeled EGF from mouse submaxillary glands (Molecular Probes Europe, Leiden, The Netherlands), washed and analyzed by flow cytometry.

Figure 3:
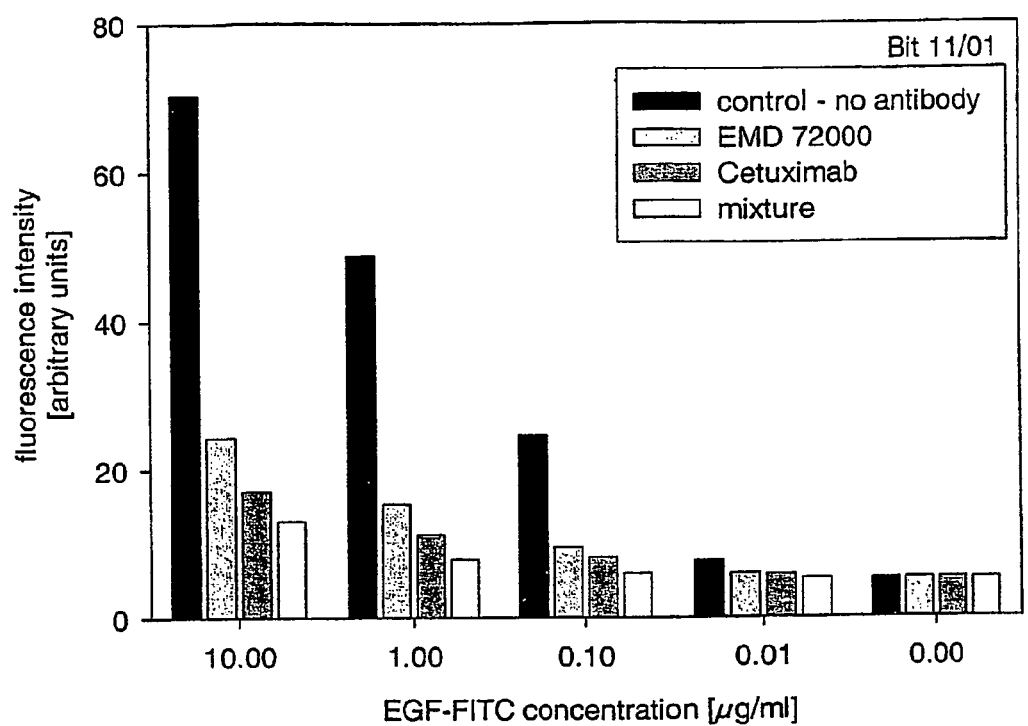
FIG. 3 shows the inhibition of EGF binding to A431 tumor cells by MAb 425, MAb 225, or a mixture of both.
Figure 4:
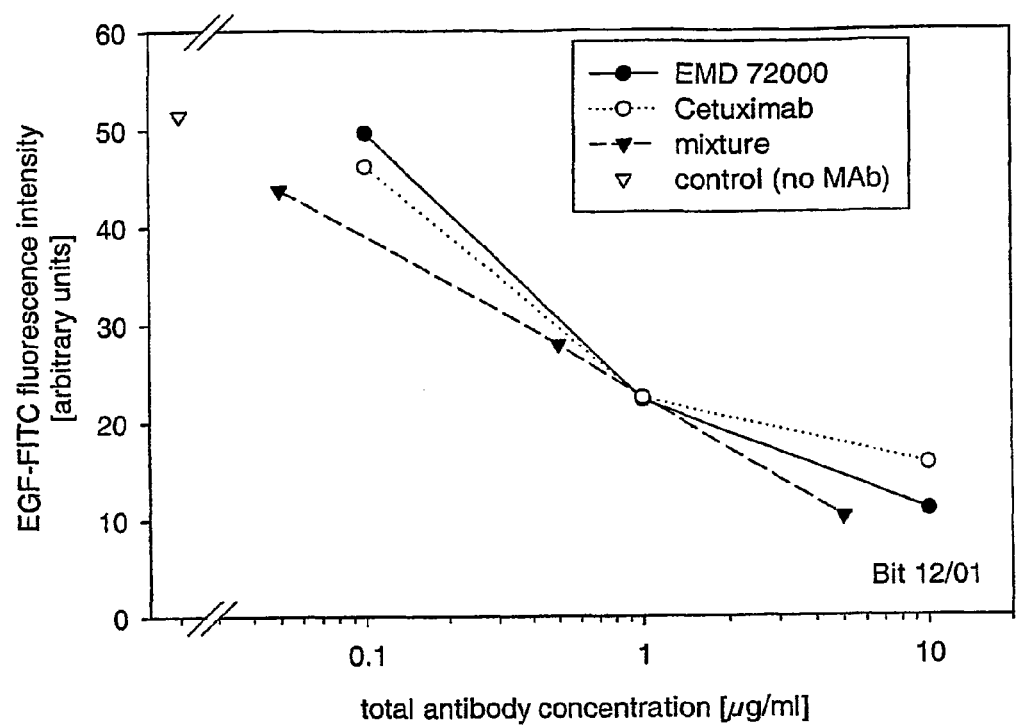
FIG. 4 depicts the displacement of bound EGF on A431 cancer cells by MAb 425, MAb 225, or a mixture of both.

Both antibodies strongly inhibited binding of EGF-FITC at all concentrations. The mixture of both antibodies however was more effective than either antibody alone in all cases (FIG. 3).

Example 4

Displacement Bound EGF from EGFR of A431 Cells.

A431 cells were preincubated for 15 minutes on ice with 10 µg/ml FITC-labeled EGF from mouse submaxillary glands (Molecular Probes Europe, Leiden, The Netherlands). Thereafter cells were washed and incubated for 15 minutes with 10, 1 or 0.1 µg/ml of EMD 72 000 or Cetuximab, respectively, or with a mixture of 2.5, 0.25 or 0.025 µg/ml of both antibodies (total immunoglobulin concentration: 5, 0.5 or 0.05 µg/ml). Cells were then washed and analyzed by flow cytometry for bound EGF-FITC.

Both antibodies as single agents in a concentration-dependent manner displaced EGF from EGFR of A431 cells. The mixture of both antibodies, which contained only one fourth of the antibody concentrations (½ of total immunoglobulin) of each MAb, was similarly effective in displacement of the FITC-labeled ligand than each of both antibodies at a higher concentration.

Example 5

Down-Modulation of EGFR by a Mixture of at Least Two Antibodies Against Different Receptor Epitopes but No or Only Minor Reduction of Cell Surface EGFR Levels by One Single Antibody After a 24-Hours Incubation of A431 Cells with MAbs.

Figure 5:
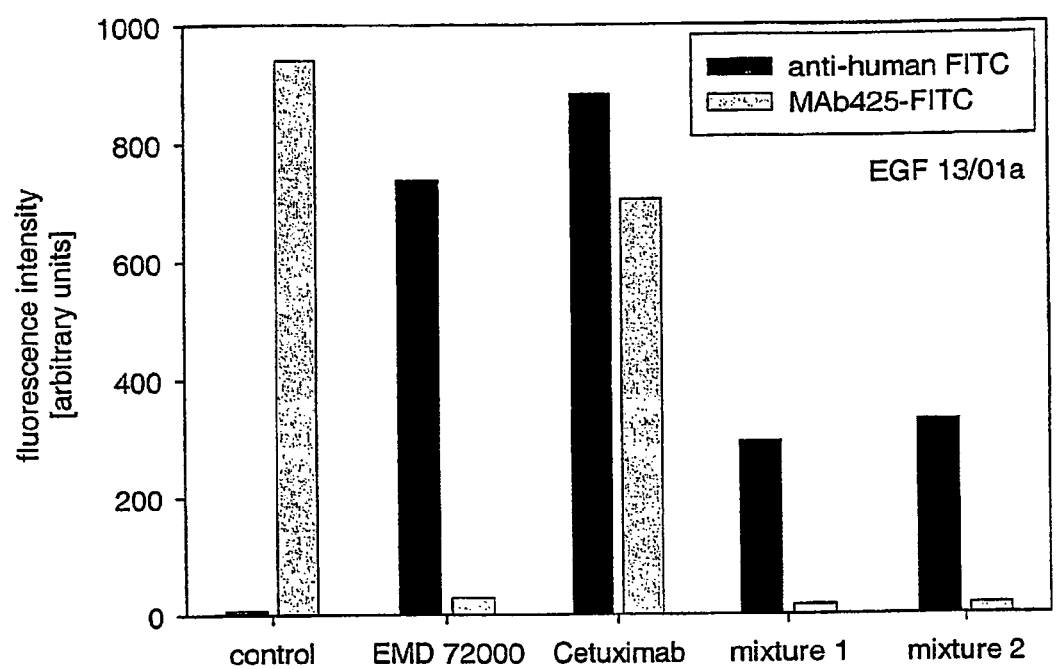
FIG. 5 shows the down-modulation of EGF receptor on A431 cells by a mixture of humanized MAb 425 (EMD 72000) and chimeric MAb 225.

$2\times10^6$ A431 cells in 2.5 ml medium containing 10% FCS (fetal calf serum) were seeded into wells of 6-well microplates. Antibodies (Cetuximab, EMD 72 000) were added to the cultures at a final concentration of 10 µg/ml. Mixtures of both antibodies were used at final concentrations for each antibody of 10 µg/ml (mixture 1) or 5 µg/ml (mixture 2), resulting in a total antibody concentration of 20 and 10 µg/ml respectively. Cells were then incubated in the presence of the antibodies for 24 hours at 37° C. and 10% $CO_2$. Thereafter cells were harvested by Trypsin/EDTA (0.05/0.02%) treatment, washed and incubated for 15 minutes on ice with either 20 µg/ml FITC-labeled goat anti-human IgG+IgM(H+L)-F(ab')$_2$ as 2nd step reagent for detection of surface-bound anti-EGFR antibodies or 10 µg/ml of FITC-labeled MAb425 (murine predecessor of EMD 72 000) for detection of free, non-occupied binding-sites for EMD 72 000. Finally cells were analyzed by flow cytometry. FIG. 5 demonstrates that EMD 72 000 and its murine predecessor MAb425 compete for binding to their epitopes on EGFR and that pre-bound EMD 72 000 nearly completely can inhibit binding of MAb425-FITC. In contrast to this, pre-bound Cetuximab only minimally inhibits binding of MAb425-FITC compared to untreated control cells. This clearly indicates that both antibodies bind to distinct epitopes of EGFR. Furthermore this figure shows that after incubation of cells for 24 hours in presence of both concentrations of the antibody mixture the fluorescence intensity of FITC-labeled 2nd step reagent used for detection of surface-bound antibodies is clearly reduced.

This indicates that surface EGFR levels of cells treated with the antibody mixture are clearly reduced compared to cells that were cultured with only one of the antibodies. Thus, larger receptor-antibody complexes formed by the mixture of MAbs seem to be internalized and/or processed by other mechanisms than small receptor-antibody complexes consisting of only two receptors after cross-linking by one antibody molecule.

We claim:

1. A pharmaceutical composition comprising a first antibody or a binding fragment thereof and a second antibody or a binding fragment thereof, having the capability to bind to different epitopes located on an ErbB1 receptor molecule, wherein said first antibody molecule or a portion thereof comprises a binding site that bind to a first specific epitope on the ErbB1 receptor molecule, and said second antibody molecule comprises a binding site that binds to a second specific different epitope on said ErbB1 receptor molecule, wherein said first and said second epitopes on the ErbB1 receptor molecule are located within the ErbB1 receptor ligand-binding domain, thereby increasing the amount of antibody bound per receptor and per cell by the same antibody dose and causing an enhanced ErbB1 blocking or inhibition and induction of down-regulation of ErbB1 receptor-specific pathway signaling as compared with a composition comprising said first or second antibody molecule only, wherein said first antibody is humanized MAb 425 (h425) and said second antibody is chimeric MAb 225 (c225).

2. The pharmaceutical composition according to claim 1, wherein said receptor ligand-binding domain is the binding domain of the natural ligand of said ErbB1 receptor.

3. The pharmaceutical composition according to claim 1, wherein said composition exhibits enhanced induction of cross-linking and/or dimerization of ErbB1 receptor molecule compared to a composition comprising a single antibody molecule which binds to said first or said second epitope on said ErbB1 receptor molecule.

4. The pharmaceutical composition according to claim 1, further comprising a cytotoxic agent.

5. The pharmaceutical composition according to claim 4, wherein said cytotoxic agent is a chemotherapeutic agent.

6. The pharmaceutical composition according of claim 5, wherein said chemotherapeutic agent is cisplatin, doxorubicin, gemcitabine, docetaxel, paclitaxel, or bleomycin.

7. The pharmaceutical composition according of claim 4, wherein said cytotoxic agent is an ErbB receptor inhibitor, a VEGF receptor inhibitor, a tyrosine kinase inhibitor, a protein kinase A inhibitor, an anti-angiogenic agent, or a cytokine.

8. A kit comprising the pharmaceutical composition of claim 1 in one package and a carrier in a second package.

9. A method of inhibiting tumor growth and/or metastasis comprising contacting said tumor with the pharmaceutical composition according of claim 1.

10. The method according to claim 9, wherein the tumor is breast cancer, prostate cancer, head and neck cancer, SCLC or pancreas cancer.

\* \* \* \* \*

UNITED STATES PATENT AND TRADEMARK OFFICE
CERTIFICATE OF CORRECTION

PATENT NO. : 7,638,125 B2
APPLICATION NO. : 10/530871
DATED : December 29, 2009
INVENTOR(S) : Kreysch et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 367 days.

Signed and Sealed this

Ninth Day of November, 2010

David J. Kappos
*Director of the United States Patent and Trademark Office*